(12) United States Patent
Shibuya et al.

(10) Patent No.: US 8,437,534 B2
(45) Date of Patent: May 7, 2013

(54) DEFECT CLASSIFICATION METHOD AND APPARATUS, AND DEFECT INSPECTION APPARATUS

(75) Inventors: Hisae Shibuya, Chigasaki (JP); Shunji Maeda, Yokohama (JP); Akira Hamamatsu, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1080 days.

(21) Appl. No.: 11/779,905

(22) Filed: Jul. 19, 2007

(65) Prior Publication Data
US 2008/0075352 A1   Mar. 27, 2008

(30) Foreign Application Priority Data
Sep. 27, 2006   (JP) ................................ 2006-262083

(51) Int. Cl.
G06K 9/00 (2006.01)
G06K 9/68 (2006.01)
G05B 13/02 (2006.01)
G06F 7/00 (2006.01)
G06F 17/00 (2006.01)

(52) U.S. Cl.
USPC ............. 382/149; 382/226; 700/28; 707/797; 706/47

(58) Field of Classification Search .................. 382/141, 382/149, 226; 707/797; 700/28; 706/47
See application file for complete search history.

(56) References Cited

U.S. PATENT DOCUMENTS

| 5,032,727 A * | 7/1991 | Cox et al. .................... 250/330 |
| 2004/0181553 A1* | 9/2004 | Stockfisch ................. 707/104.1 |
| 2006/0288031 A1* | 12/2006 | Lee ............................... 707/101 |

FOREIGN PATENT DOCUMENTS

| JP | 2002-257533 | 9/2002 |
| JP | 2004-047939 | 2/2004 |
| JP | 2006-300517 | 11/2006 |

* cited by examiner

*Primary Examiner* — Kathleen Y Dulaney
(74) *Attorney, Agent, or Firm* — Antonelli, Terry, Stout & Kraus, LLP.

(57) ABSTRACT

A defect classification method to classify defects by using a classifier having a binary tree structure based on features of defects extracted from detected signals acquired from a defect inspection apparatus includes a classifier construction process for constructing the classifier by setting a branch condition including defect classes respectively belonging to groups located on both sides of the branch point, a feature to be used for branching, and a discriminant reference, for each branch point in the structure based on instruction of defect classes and feature data respectively associated therewith beforehand. The process includes a priority order specification process for previously specifying target classification performance of purity and accuracy for each defect class, whole and in worst case, with priority order, and an evaluation process for evaluating whether the specified target classification performance under the branching condition is satisfied and displaying a result of evaluation, every item.

16 Claims, 19 Drawing Sheets

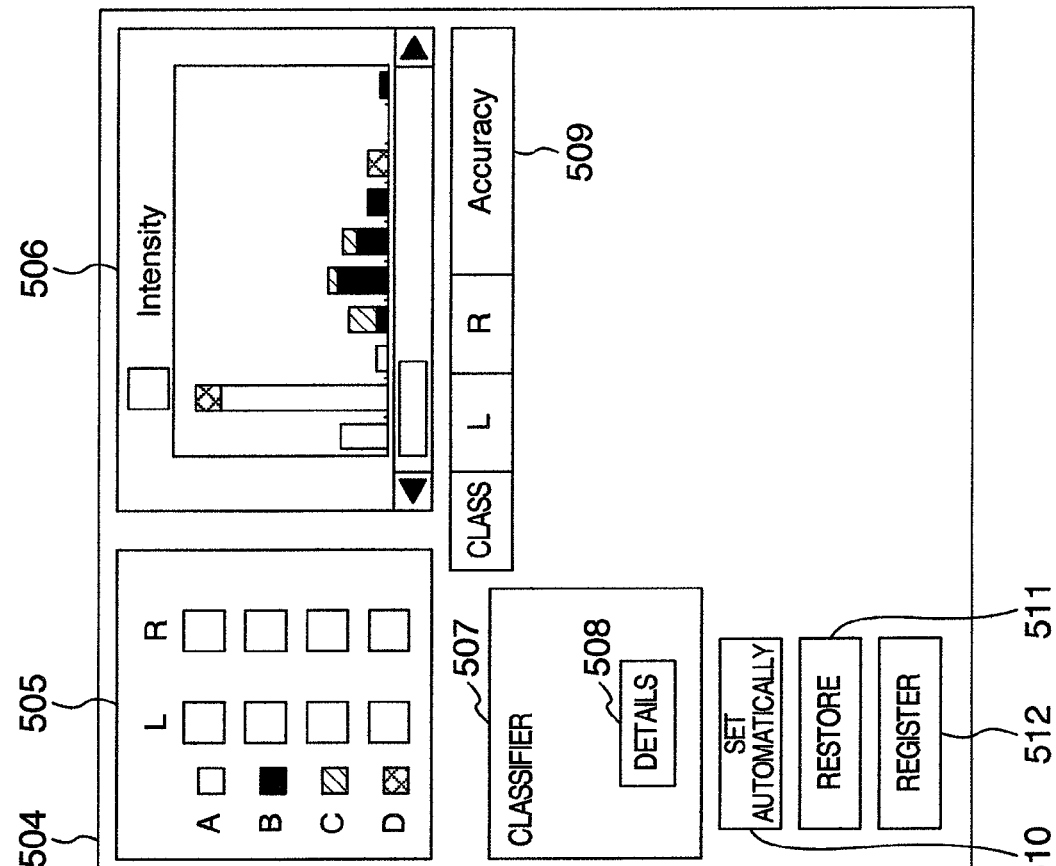
FIG.8C
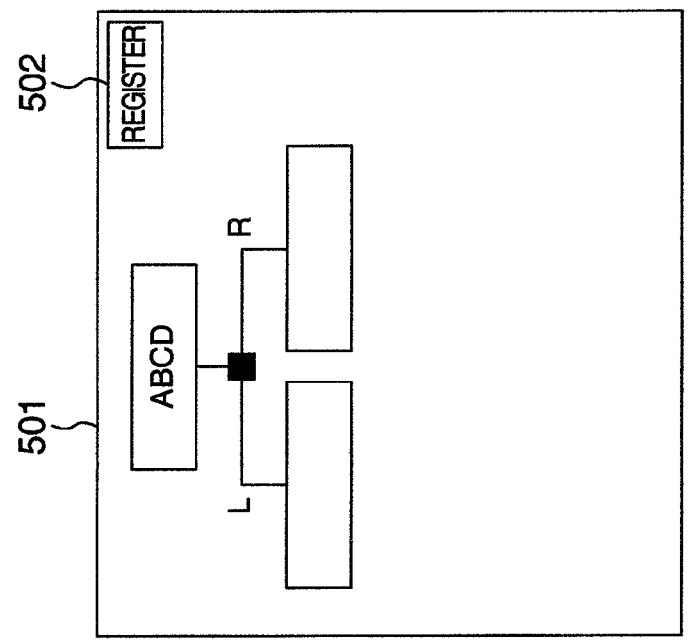
FIG.8A
FIG.8B

L  A
R  BCD

FEATURE α

0.41

MAXIMUM

FEATURE β  - - - -

0.07

L  AB
R  CD 0.33

FREQUENCY 0.06

DEGREE OF SEPARATION

VALUE OF FEATURE

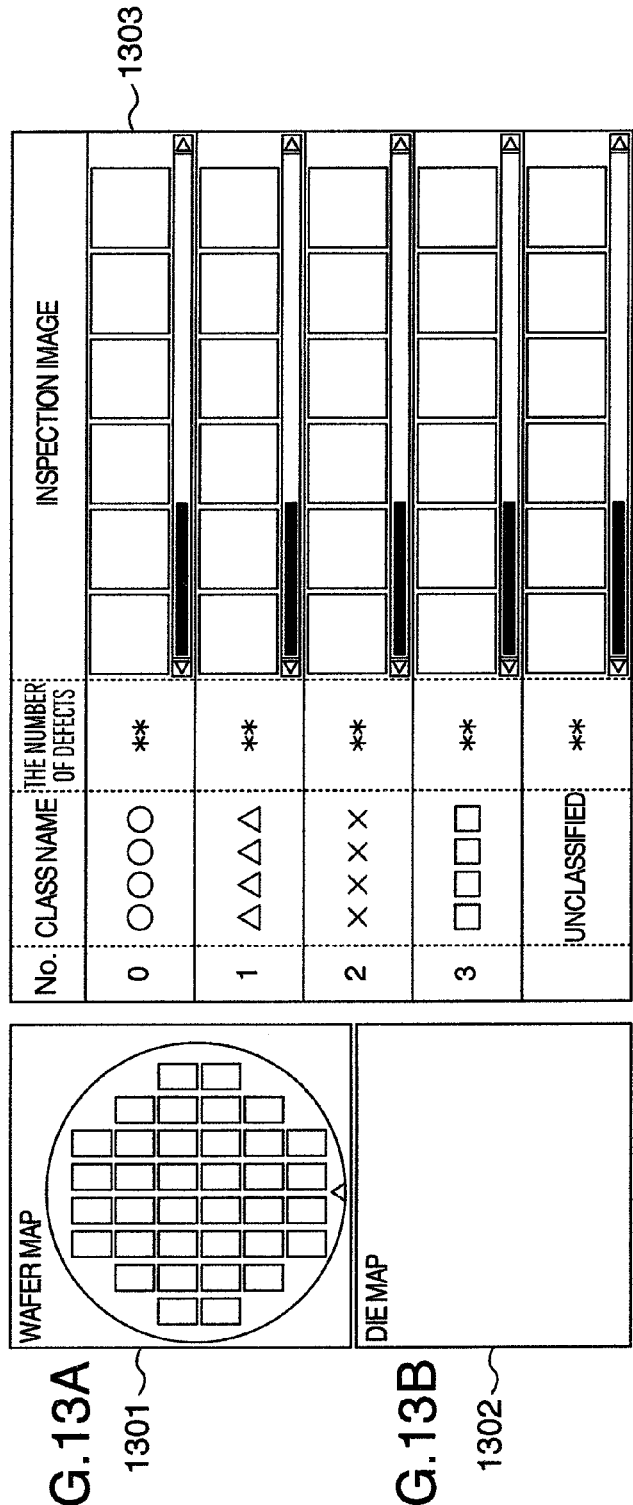
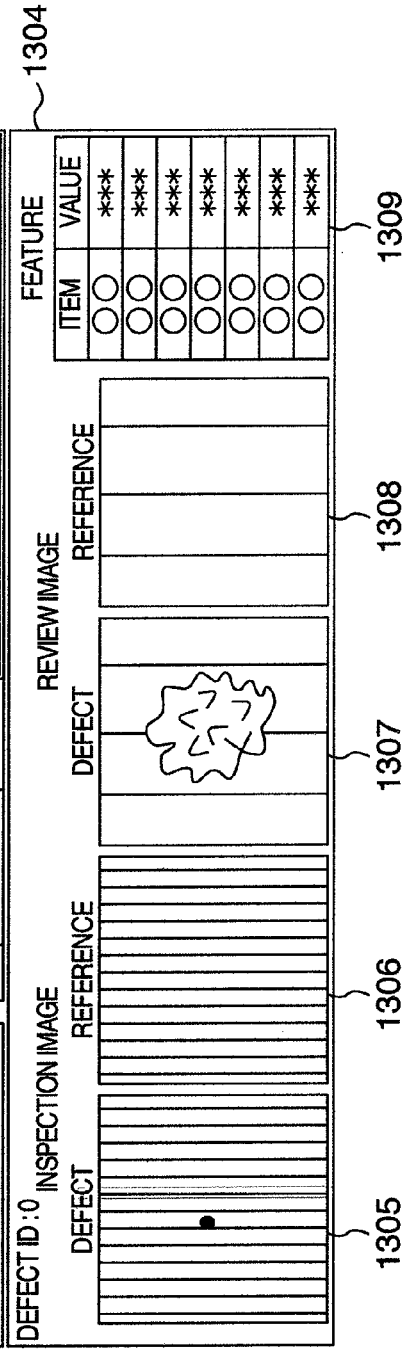
FIG. 13A
FIG. 13B
FIG. 13C
FIG. 13D

FIG. 18

SATISFACTION DEGREE EVALUATION RESULT — 1701

| ORDER | DEFECT CLASS | A/P | TARGET | RESULT | DIFFERENCE | DECISION |
|---|---|---|---|---|---|---|
| 1 | C 21 PATTERN DEFECT | Purity | 90% | 98.0% | +8.0% | OK |
| 2 | C 21 PATTERN DEFECT | Accuracy | 90% | 98.0% | +8.0% | OK |
| 3 | D 31 HOLLOW | Purity | 80% | 60.0% | −20.0% | NG |
| 4 | Minimum | Accuracy | 60% | 48.6% | −11.4% | NG |
| 5 | All | Accuracy | 80% | 81.2% | +1.2% | OK |

— 1702

CONFUSION MATRIX — 1703

|   | A | B | C | D | Accuracy |
|---|---|---|---|---|---|
| A | 33 | 2 | 0 | 0 | 94.3% |
| B | 2 | 52 | 0 | 11 | 80.0% |
| C | 0 | 0 | 48 | 1 | 98.0% |
| D | 5 | 13 | 1 | 18 | 48.6% |
| Pu. | 82.5% | 77.6% | 98.0% | 60.0% | 81.2% |

1 ○  2 ○
3 ×  4 ×
      5 ○

[REGISTER] — 1704
[END] — 1705

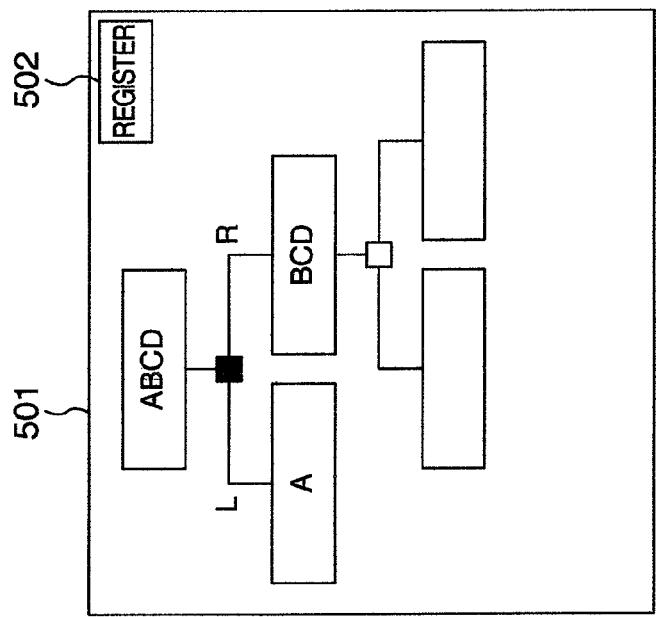

FIG.21A
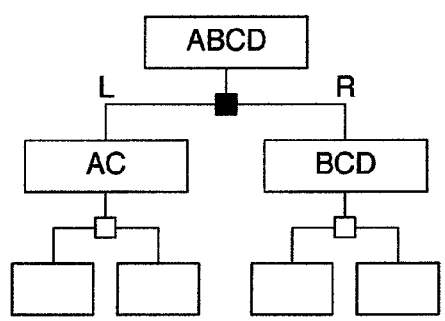
FIG.21B
| CLASS | | L | R | Opp | Accuracy | |
|---|---|---|---|---|---|---|
| L | | 17 | 5 | 0 | 77.3% | 4 ○ |
| | A | 13 | 5 | 0 | 72.2% | |
| | C | 4 | – | 0 | 100% | |
| R | | 3 | 38 | 0 | 92.7% | |
| | B | 1 | 10 | 0 | 90.9% | |
| | C | – | 9 | 0 | 100% | 2 ○ |
| | D | 2 | 19 | 0 | 90.5% | |
| Opp | | 0 | 0 | 0 | – | |
| Purity | | 85 | 88 | – | 87.3% | 5 ○ |
FIG.21C
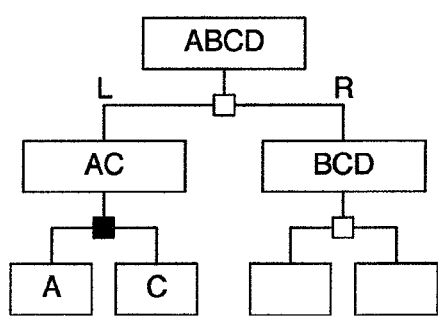
FIG.21D
| CLASS | | L | R | Opp | Accuracy | |
|---|---|---|---|---|---|---|
| L | | 11 | 2 | 5 | 61.1% | 4 ○ |
| | A | 11 | 2 | 5 | 91.1% | |
| R | | 0 | 4 | – | 100% | |
| | C | 0 | 4 | – | 100% | 2 ○ |
| Opp | | 2 | 1 | 38 | – | |
| | B | 1 | 0 | 10 | 90.9% | |
| | C | – | – | 9 | 100% | |
| | D | 1 | 1 | 19 | 90.5% | |
| Purity | | 85 | 81 | – | 84.1% | 5 ○ |
1 ×

DEFECT CLASSIFICATION METHOD AND APPARATUS, AND DEFECT INSPECTION APPARATUS

INCORPORATION BY REFERENCE

The present application claims priority from Japanese application JP2006-262083 filed on Sep. 27, 2006, the content of which is hereby incorporated by reference into this application.

BACKGROUND OF THE INVENTION

The present invention relates to a defect classify and inspection method, and apparatus, to classify defects such as minute pattern defects and dust particles on the basis of an image of an inspection subject obtained from a thin film device such as a semiconductor wafer, a TFT or a photomask by using lamp light, laser light or an electron beam. In particular, the present invention relates to a defect inspection method, and apparatus, suitable for inspecting defects in a semiconductor wafer.

Thin film devices such as semiconductor wafers, liquid crystal displays and hard disk magnetic heads are manufactured through a large number of working processes. In the manufacture of such thin film devices, visual inspection is executed every some series of processes with the object of yield improvement and stabilization. In the visual inspection, defects such as pattern defects or dust particles are detected on the basis of a reference image and an inspection image obtained respectively from corresponding regions of two patterns formed originally so as to have the same shape by using lamp light, laser light or an electron beam. In other words, the reference image is aligned with the inspection image to calculate a difference, and the difference is compared with a separately determined threshold to detect a part having a large difference as a defect or a dust particle. At the same time, features, such as the luminance and size, of a defect are calculated from an image of the defect part and the defect is sorted on the basis of the features, in some cases.

For example, an inspection apparatus that sorts a dust particle which is a convex defect and a scratch which is a concave defect according to a difference in scattered light intensity caused by vertical illumination and oblique illumination is disclosed in JP-A-2002-257533 (Patent Document 1). When determining a defect sort condition of the inspection apparatus having such a defect sort function, it is necessary to instruct a class to be sorted into by using a review and derive a relation between features and the class. In the above-described example, the class to be sorted into is either a dust particle or a scratch. The scattered light intensity under the vertical illumination and the scattered light intensity under the oblique illumination are used as the features. A discriminant line is set manually on the basis of a two-dimensional scatter diagram.

In addition, there are instruction type and rule base type in sort techniques. In the instruction type, a sorter is automatically constructed by instruction of feature data associated with a correct answer class. In a method used in sort of the instruction type, a defect is sorted into a class of already taught defects having a shortest distance in the feature space. In another method used in sort of the instruction type, feature distribution of each defect class is presumed on the basis of instruction data and a defect is sorted into a class in which the occurrence probability of the features of a defect to be sorted is the highest. The rule base type is a method of sorting defects according to a rule described in the "if-then-else" form. In many cases, the rule is represented by a threshold for a feature. The classify method described in Patent Document 1 is also a kind of the rule base type.

A method for generating a defect classifier described in JP-A-2004-47939 (Patent Document 2) includes an inspection information acquisition step of inspecting a defective sample group on an arbitrary sample by using at least an arbitrary defect inspection apparatus and acquiring sample inspection information, and a decision tree setting step. The decision tree setting step includes a display step of displaying a state of defect attribute distribution of a defective sample group on the arbitrary sample, on a screen on the basis of the sample inspection information acquired at the inspection information acquisition step. The decision tree setting step further includes a classify rule setting step of setting an individual classify rule for each of branch elements in a decision tree, which hierarchically develops sort class elements of the defective sample group via branch elements, on the basis of the state of the defect attribute distribution displayed on the screen.

SUMMARY OF THE INVENTION

The defect sort of the rule base type has an advantage that classify condition setting with a user's intention reflected therein on the basis of the theory and experience is possible and the user can easily understand the classify condition setting. However, the defect classify of the rule base type has a problem that it is difficult to set all of the classify condition manually if feature kinds or defect class kinds have increased.

On the other hand, in the defect classify of the instruction type, the classify condition is automatically set if data is input. However, the defect classify of the instruction type has a problem that the user's intention cannot be reflected and the classify condition cannot be interpreted, either. The user's intention is, for example, to conduct adjustment so as to make the purity, accuracy or both of them equal to at least a target value(s), to intentionally avoid use of a certain feature, or to determine features to be used, on the basis of knowledge.

In order to solve the above-described problems, the present invention provides a defect classification method, and apparatus, and a defect inspection apparatus that makes it possible to classify defects by using a binary tree structure or an instruction type classifier having a classify condition setting function that can reflect the user's intention.

In accordance with the present invention, in a defect classification method, and apparatus, to classify defects by using a classifier having a binary tree structure on the basis of features of the defects extracted on the basis of detected signals acquired from a defect inspection apparatus includes a classifier construction process for constructing the classifier having the binary tree structure by setting a branch condition for each branch point in the binary tree structure on the basis of instruction of defect classes and feature data respectively associated therewith beforehand, the branch condition including defect classes respectively belonging to groups located on both sides of the branch point, a feature to be used for branch, and a discriminant reference. In the classifier having the binary tree structure, defects are finally classified into desired classes by repetitively bisecting defect data. The branch condition setting at each branch point includes a step of determining details of classes to be bisected, a step of determining a feature to be used for branch, and a step of determining a discriminant reference (classify reference) such as a threshold or probability distribution.

In accordance with the present invention, the classifier construction process can use both automatic setting and manual setting as the branch condition setting. In other words, as for branch condition setting, three steps are executed automatically, or details are determined manually and remaining steps are executed automatically, or details and features are set manually and remaining steps are executed automatically, or all three steps are set manually. In the configuration, any of them can be selected. In the configuration, it is also possible to conduct conduction setting automatically at a selected branch point and the subsequent structure.

In accordance with the present invention, the classifier construction process includes a display process for displaying information that represents feature distribution by defect classes and information that represents an evaluation result of classify performance under the set branch condition, every branch point in the binary tree structure. In other words, manual setting is supported by a configuration that displays a histogram by defect classes and correct answer ratios by defect classes with respect to a specified branch point.

In accordance with the present invention, the classifier construction process includes a priority order specification process for previously specifying target sort performance of purity and accuracy for each of defect classes, whole and in worst case, with priority order; and an evaluation process for evaluating whether the specified target sort performance under the set branch condition is satisfied every item and displaying a result of evaluation every item. In other words, a function of conducting specification with priority order as the user's intention is provided. It is evaluated and displayed with respect to a specified branch point whether each of items of the user's intention is satisfied.

In accordance with the present invention, a defect classification method, and apparatus, to classify defects by using a classifier of instruction type (a classify algorithm of instruction type) on the basis of features of the defects extracted on the basis of detected signals acquired from a defect inspection apparatus includes a priority order specification process for previously specifying target sort performance of purity and accuracy for each of defect classes, whole and in worst case, with priority order; and a sorter construction process for constructing the classifier of instruction type by setting a classify condition by means of learning using a learning algorithm and a learning parameter specified beforehand, on the basis of instruction of defect classes and feature data respectively associated therewith beforehand. In the classifier construction process, classification performance under the set classify condition is evaluated and whether the specified target classification performance is satisfied is displayed every item.

In accordance with the present invention, a defect classification method, and apparatus, to classify defects by using a classifier of instruction type (a classify algorithm of instruction type) on the basis of features of the defects extracted on the basis of detected signals acquired from a defect inspection apparatus includes a priority order specification process for previously specifying target sort performance of purity and accuracy for each of defect classes, whole and in worst case, with priority order; and a sorter construction process for constructing the classifier of instruction type by evaluating whether the specified target sort performance is satisfied every item while comprehensively changing a learning algorithm and a learning parameter of the classifier of instruction type on the basis of instruction of defect classes and feature data respectively associated therewith beforehand, searching for a learning algorithm and a learning parameter that are favorable in a result of evaluation conducted every item, and setting a classify condition on the basis of learning using the learning algorithm and learning parameter obtained by the searching.

In accordance with the present invention, the features to classify defects by using the classifier are obtained by unifying features of defects extracted on the basis of detected signals acquired by respective inspections under a plurality of different conditions in the defect inspection apparatus, after conducting matching of defect coordinates.

In accordance with the present invention, when sorting defects by using a classifier on the basis of the features of the defects, defect classes are determined by individually using features of the defect extracted on the basis of detected signals acquired by respective inspections under a plurality of different conditions in the defect inspection apparatus, individually making defect classify decisions according to a plurality of defect classify conditions preset for the classifier, and unifying results of the individual defect classify decisions by means of weighted voting of reliability.

These and other objects, features and advantages of the invention will be apparent from the following more particular description of preferred embodiments of the invention, as illustrated in the accompanying drawings.

BRIEF DESCRIPTION OF THE DRAWINGS

FIGS. 8A, 8B and 8C are a diagram showing a display state of a GUI given when classify condition setting is started, according to the present invention;

FIGS. 13A to 13D are a diagram showing an embodiment of a GUI for instructing a defect class in a classify condition setting unit included in classifier construction means according to the present invention;

FIG. 18 is a diagram showing a second embodiment of a GUI that displays a satisfaction evaluation result of user's intention in classify condition setting for constructing (generating) a classifier (classify algorithm) of instruction type according to the present invention;

FIGS. 20A, 20B and 20C are a diagram showing a second embodiment of a GUI that displays a satisfaction evaluation result of user's intention in classify condition setting for constructing (generating) a classifier having a binary tree structure according to the present invention;

FIGS. 21A-21D are a diagram for explaining an embodiment of a modification method of a binary tree branch condition according to the present invention.

DESCRIPTION OF THE EMBODIMENTS

Embodiments of a defect classification method, and apparatus, and a defect inspection method, and apparatus, having a sort condition setting function capable of reflecting user's intention, according to the present invention will be described with reference to the drawings.

First Embodiment

The first embodiment of a defect classification method, and apparatus, and a defect inspection method, and apparatus, in which defects are classified by using a classifier constructed (generated) with a classify condition setting function according to the present invention will be described in detail with reference to FIGS. 1 to 15.

Figure 1:
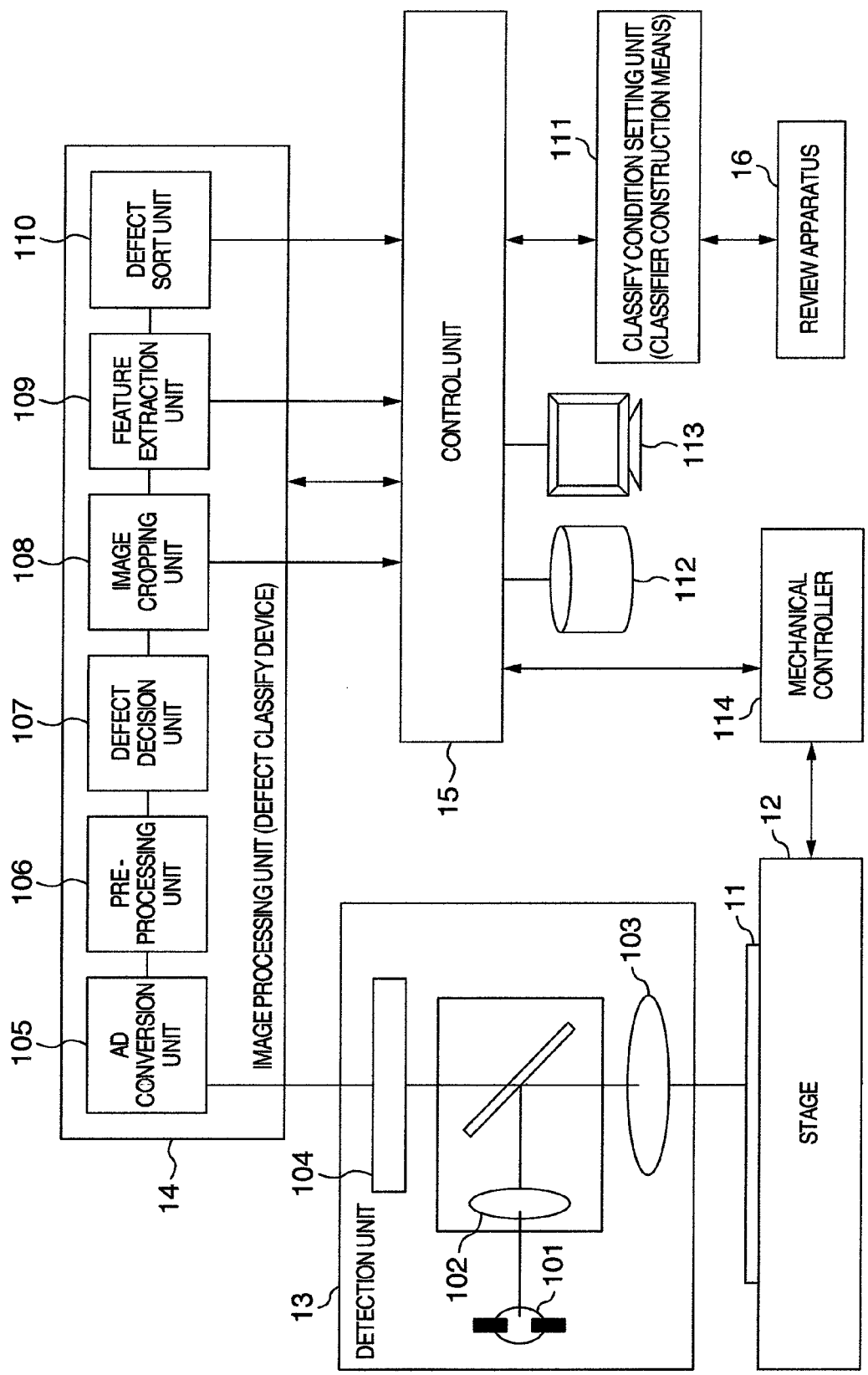
FIG. 1 is a schematic configuration diagram showing an embodiment of a defect inspection apparatus (visual inspection apparatus) according to the present invention.

As the first embodiment, the case of an optical defect inspection apparatus (optical visual inspection apparatus) for semiconductor wafers will be described. FIG. 1 shows an embodiment of a configuration of the optical defect inspection apparatus. The first embodiment is not restricted to optical defect inspection apparatuses, but is applicable to electron beam type defect inspection apparatuses or the like, as well.

Reference numeral 11 denotes an inspection subject such as a semiconductor wafer. Reference numeral 12 denotes a stage for mounting and moving the inspection subject 11. Reference numeral 13 denotes a detection unit. The detection unit 13 includes a light source 101 for irradiating the inspection subject 11, an illumination optical system 102 for condensing light emitted from the light source 101, an object lens 103 for forming an optical image obtained by illuminating the inspection subject 11 with illumination light condensed by the illumination optical system 102 resulting in reflection, and an image sensor 104 for converting the formed optical image to an image signal according to brightness. Reference numeral 14 denotes an image processing unit, which detects defect candidates on a wafer serving as a sample by using an image detected by the detection unit 13. The light source 101 is, for example, a lamp light source or a laser light source. The image sensor 104 is, for example, a CCD linear sensor, a TDI sensor or a photomultiplier.

The image processing unit 14 includes an AD conversion unit 105 for converting an input signal supplied from the image sensor 104 in the detection unit 13 to a digital signal, a pre-processing unit 106 for conducting image correction such as shading correction and dark level correction on the digital signal obtained by the AD conversion, a defect decision unit 107 for comparing a reference image detected from a corresponding position in an adjacent die with a detected image and outputting a portion where a difference value is greater than a separately set threshold as a defect, an image cropping unit 108 for extracting the detected image and the reference image with a predetermined size around a position of the detected defect, a feature extraction unit 109 for extracting (calculating) features of the defect from the cropped image, and a defect sort unit 110 for sorting the defects by using a classifier having a binary tree structure or a classifier of instruction type on the basis of the extracted (calculated) features of the defect. The extracted features of the defect may be obtained by conducting matching of defect coordinates and unifying features of the defect extracted on the basis of detected signals which are acquired by respective inspections under a plurality of different conditions (including an optical condition and an image processing condition) in the defect inspection apparatus. When classify defects by using a classifier having a binary tree structure or a classifier of instruction type on the basis of features of the defect, it is also possible to determine defect classes by individually using features of the defect extracted on the basis of detected signals acquired by respective inspections under a plurality of different conditions (including an optical condition and an image processing condition) in the defect inspection apparatus, individually making defect sort decisions according to a plurality of defect classify conditions preset for the classifier, and unifying results of the individual defect class decisions by means of weighted voting of reliability.

Reference numeral 15 denotes a general control unit. The general control unit 15 includes a storage 112 for storing coordinates, features and an image of each of detected defects, a user interface unit 113 for accepting a change of an inspection parameter from the user and displaying detected defect information, and a CPU for exercising various controls. Reference numeral 114 denotes a mechanical controller which drives the stage 12 on the basis of a control command given by the general control unit. Although not illustrated, the image processing unit 14 and the detection unit 13 are also driven by a command given by the general control unit 15. Reference numeral 111 denotes a classify condition setting unit, which sets a sort condition for determining a defect class on the basis of the features of the defect.

Reference numeral 16 denotes a review apparatus, which is not included in the inspection apparatus, but which can give and receive data.

The GUI using the classify condition setting unit 111 and the user interface unit 113 inclusive of the review apparatus is thus included in sorter construction means which constructs (generates) a sorter having a binary tree structure or a classifier of instruction type.

An embodiment of a defect detection method using the defect inspection apparatus (visual inspection apparatus) shown in FIG. 1 will now be described.

Figure 2:
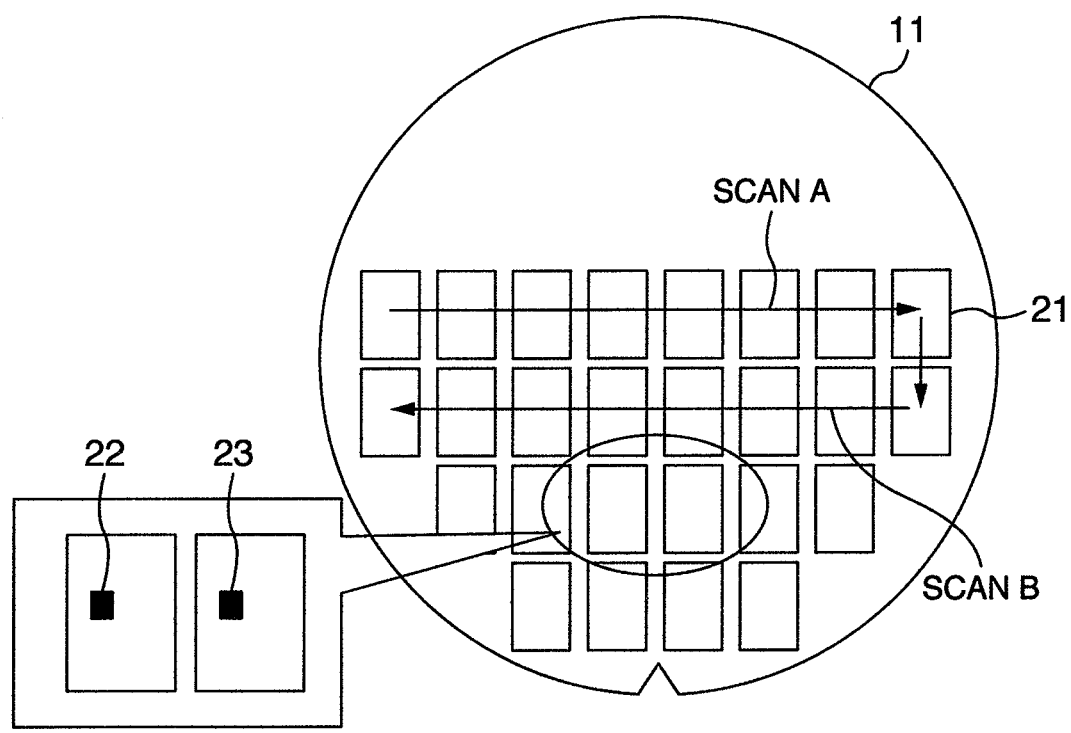
FIG. 2 is a plan view of a semiconductor wafer to be inspected, according to the present invention.

On a semiconductor wafer 11 which is the inspection subject, a large number of dies 21 that should have the same pattern are arranged regularly as shown in FIG. 2. The defect decision unit 107 in the image processing unit 107 compares images in the same position of two adjacent dies, for example, compares an image in a region 22 shown in FIG. 2 with an image in a region 23 of an adjacent chip, and detects a portion having a difference between them as a defect.

The operation will now be described. The general control unit 15 continuously moves the semiconductor wafer 11 which is the inspection subject into, for example, a direction opposite to a direction of a scan A shown in FIG. 2 by using the stage 12. In synchronism with the continuous movement of the stage 12, the image sensor 104 in the detection unit 13 detects optical images of the inspection subject 11 successively in the direction of the scan A and takes in images of the chip. The image sensor 104 in the detection unit 13 outputs the signal input thereto to the image processing unit 14. In the image processing unit 14, first, the AD conversion unit 105 converts the input analog signal to a digital signal, and then the pre-processing unit 106 conducts shading correction and dark level correction.

Figure 3:
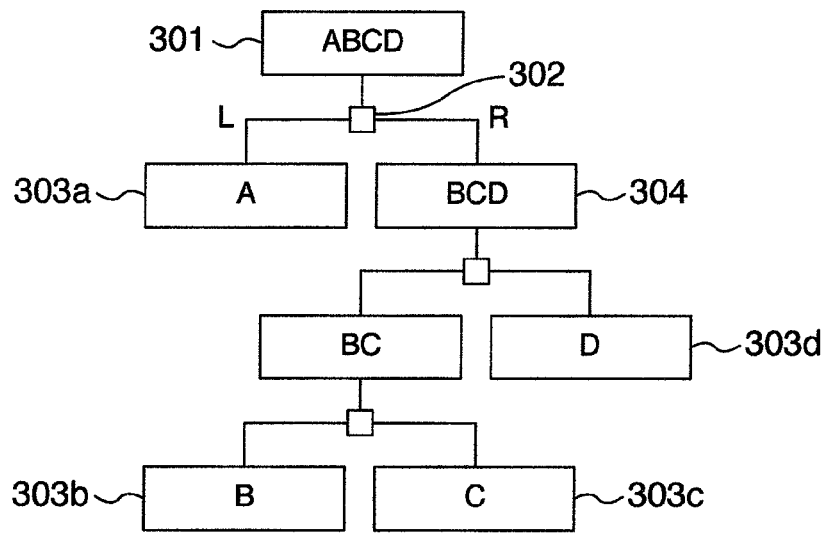
FIG. 3 is a diagram for explaining an embodiment of a structure of a classifier having a binary tree structure according to the present invention.

The defect decision unit 107 conducts a defect decision by using a method described later. The image cropping unit 108 crops a detected image, a reference image and a threshold image with a predetermined size around a position of a defect detected by the defect decision unit 107. The feature detection unit 109 calculates features oriented for defect sort, such as a feature representing a size of the defect, a feature representing brightness (gradation value) of the defect, a feature representing a shape of the defect, and a feature representing information of background, for each of a plurality of defect candidates on the basis of the extracted detected image and reference image. The defect classify unit 110 conducts classification by using a classify method (a classifier having a binary tree structure or a classifier of instruction type) constructed previously using the classifier construction means such as the sort condition setting unit 111, and outputs class information for each defect. As a first classification method, a classifier having a binary tree structure which finally classifier defects into classes by repeating the operation of dividing defects into two as shown in FIG. 3 is used. However, it is also possible to provide known discriminant techniques together and make them selectable. The image information output from the image cropping unit 108 (such as the detected image, reference image and threshold image cropped with a predetermined size around the position of the defect), features of the defect output from the feature extraction unit 109 (features oriented for defect class such as the feature representing the size of the defect, the feature representing the brightness (gradation value) of the defect, the feature representing the shape of the defect, and the feature representing the information of the background), and the defect class information output from the defect classify unit 110 are stored in the storage 112. They are also exhibited to the user via the user interface unit 113.

Operation conducted in the defect classify unit 110 according to the present invention will now be described in detail with reference to FIG. 3. FIG. 3 schematically shows a structure of the sorter having the binary tree structure. All defect classes are included in a root node 301. At a branch point 302, defects are divided into two nodes: a left (L) node 303a and a right (R) node 304 on the basis of a predetermined branch condition. Such a branch operation is repeated and defects are finally sorted into defect classes 303a to 303d. A branching condition is set for each branch point. In the simplest case, one feature is selected and a threshold is set. If the feature is less than the threshold, the defect is classified into the left group. If the feature is at least the threshold, the defect is classified into the right group. It is also possible to select a plurality of features, set thresholds respectively for the features, and set conditions by using logical expressions. As a method to classify defects into two groups, the known two-class discriminant technique such as the support vector machine may also be adopted.

Operation conducted in the classify condition setting unit 111 included in the classifier construction means according to the present invention will now be described with reference to FIGS. 4 to 8.

Figure 4:
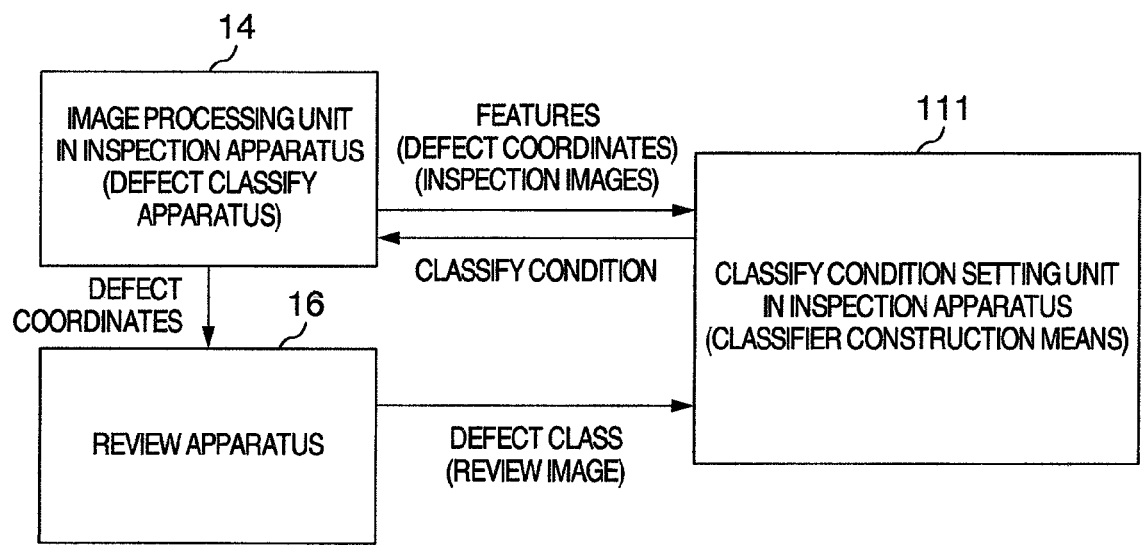
FIG. 4 is a diagram for explaining an embodiment of a flow of data of a classify condition setting unit included in classifier construction means according to the present invention.
Figure 5:
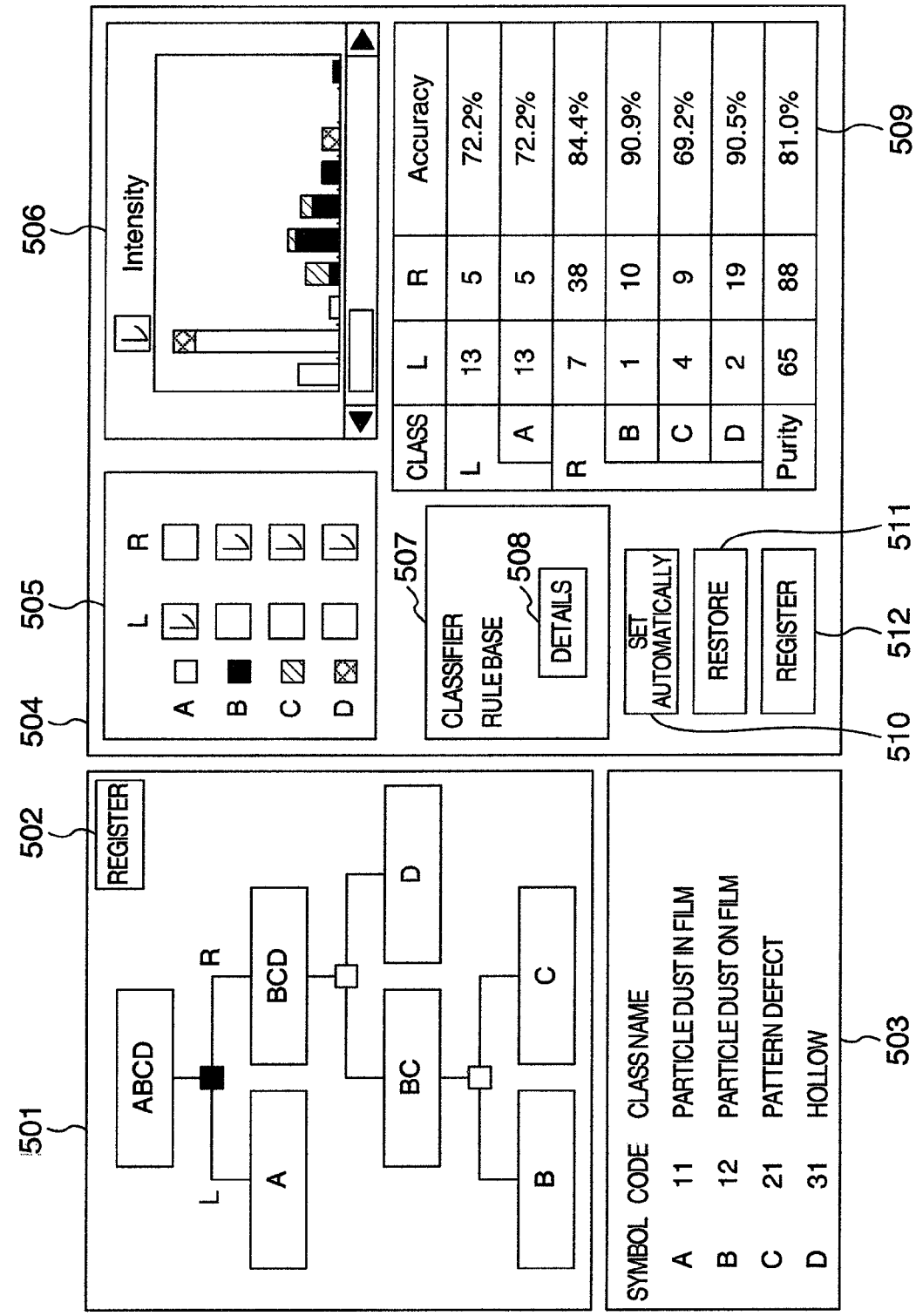
FIGS. 5A, 5B and 5C are a diagram showing a first embodiment of a classify condition setting GUI included in classifier construction means according to the present invention.

FIG. 4 shows a flow of data for the classify condition setting unit 111. The image processing unit 14 in the inspection apparatus outputs coordinates, features and a detected image of each of detected defects. The review apparatus 16 conducts review and classifies on the basis of coordinates of defects and outputs classes and review images of the defects. The classify condition setting unit 111 sets a classify condition on the basis of instruction data obtained by associating features of defects output from the image processing unit 14 with defect classes output from the review apparatus 16, and outputs the classification condition thus set.

FIGS. 5A, 5B and 5C show an embodiment of a classification condition setting GUI using the user interface unit 113 in the classification condition setting unit 111. The binary tree structure shown in FIG. 3 is displayed in a tree structure display window 501. A branch point indicated by a small square is selected by performing double click on the branch point, and the selected branch point is displayed with a different color. A "register" button 502 is a button for registering a tree structure already set and branch conditions at respective branch points as a class recipe. Associations among symbols A to D, defect class codes input from the review apparatus 16, and defect class names displayed in a tree structure are displayed in a defect class list 503. Information concerning the branching condition for the branch point selected in the tree structure display window 501 is displayed in a branching condition display window 504. In a defect class selection window 505, whether a class belongs to the left side or the right side of the selected branch point is represented by a check mark. The check can be changed manually. A histogram by classes is displayed every kind of features in a feature distribution display window 506. Explanatory notes of classes are indicated at the side of symbols AB . . . in a defect class selection window 505. A feature name of defects is displayed above the histogram. A check box before the feature name indicates whether the feature is being used. The check can be changed manually. A keyword representing a classify technique such as "rule base" is displayed in a discriminant reference display window 507. A concrete discriminant reference such as, for example, "Intensity>50=<L" is displayed by depressing a "detail" button 508. Furthermore, a GUI for setting the discriminant reference manually is displayed. With respect to the whole of classes included in L, each of the classes included in L, the whole of classes included in R, and each of the classes included in R in order from above, the number of defects sorted into L according to a preset discriminant reference, the number of defects sorted into R, and a correct answer ratio (accuracy) are displayed. A purity, that is, the ratio of the number of defects in a class checked in L in the defect class selection window 505 to the number of defects classified into L according to the preset discriminant reference (65%=13/20, 88%=38/43) is displayed in a bottom line. A correct answer ratio of the whole (81.0%=51/63) is displayed in a bottom right corner. A "set automatically" button 510 is a button for displaying an automatic setting mode setting window 601 shown in FIG. 6 and executing automatic setting according to a mode which is set. A "restore" button 511 is a button for restoring all of portions changed manually and automatically on the branch condition display window 504 to their original states. A "register" button 512 is a button for registering the portions changed manually and automatically on the branch condition display window 504.

Figure 6:
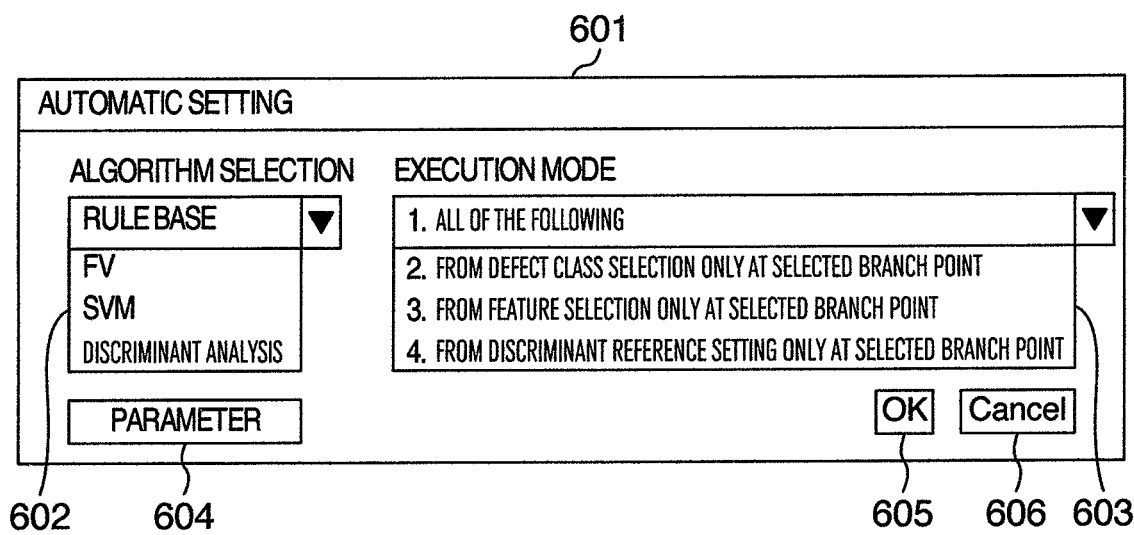
FIG. 6 is a diagram showing an embodiment of an automatic setting screen of a classify condition according to the present invention.
Figure 7:
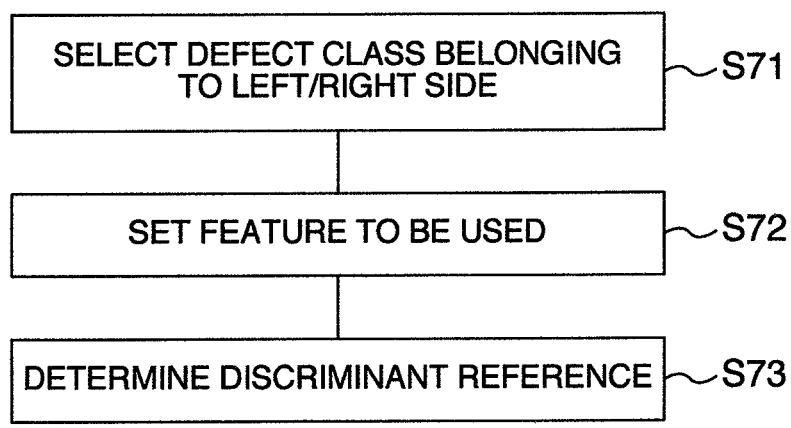
FIG. 7 is a diagram showing an embodiment of a flow of branch condition setting in the branch condition setting unit included in classifier construction means according to the present invention.

The automatic setting mode setting window 601 shown in FIG. 6 will now be described in a little more detail. An algorithm is provided to select a sort technique from among various classify techniques besides the "rule base" which is a classification technique using comparison with a threshold value. An execution mode selection list 603 is provided to specify a range for automatic setting. There are four execution modes: "1. all of the following," "2. from defect class selection only at a selected branch point," "3. from feature selection only at a selected branch point," and "4. from discriminant reference setting only at a selected branch point." In the ensuing description, they are referred to as modes 1 to 4 by using the numbers. The mode 1 is a mode for automatically setting all branch conditions inclusive of a selected branch point and the tree structure following it. The modes 2 to 4 are modes for automatically setting only at a selected branch point. A difference between them will now be described with reference to FIG. 7. FIG. 7 is a diagram showing a flow for setting a branch condition in the sort condition setting unit 111. The flow includes a step of selecting a defect belonging to the left or right group (S71), a step of selecting a feature to be used for branch (S72), and a step of determining a discriminant reference (S73). The mode 2 is a mode for setting the steps S71 to S73 automatically. The mode 3 is a mode for executing the step S71 manually and setting the steps S72 and S73 automatically. The mode 4 is a mode for executing the steps S71 and S72 manually and setting the step S73 automatically. A "parameter" button 604 is a button for setting a parameter corresponding to the selected algorithm. A parameter setting screen is displayed by depressing the "parameter" button 604, and editing can be conducted. An "OK" button 605 is a button for executing the selected algorithm and automatic setting according to the execution mode and conducting termination. A "cancel" button 606 is a button for conducting termination without executing the automatic setting.

A procedure for conducting the classify condition setting by using the GUI shown in FIGS. 5A, 5B and 5C will now be described. FIGS. 8A, 8B and 8C show a display state of the GUI at the time when starting the classify condition setting. It is supposed that defect feature data and defect class information have been associated with each other and input to the sort condition setting unit 111 as instruction data. The root node and the first branch point are displayed in the selected state in the tree structure display window 501 (FIG. 8A). Class codes and class names of all defect classes that can be read from the input information are displayed in the defect class list 503 (FIG. 8B). A symbol (ABCD) corresponding to all defect classes is displayed in the root node. Although symbols corresponding to all defect classes are displayed in the defect class selection window 505 (FIG. 8C), check is given nowhere. A histogram by classes is calculated with respect to all features and displayed in the feature distribution display window 506. Check is given nowhere. Nothing is displayed in the discriminant reference display window 507 and an evaluation window 509.

Hereafter, a procedure for setting the classify condition manually will be described. First, defect classes belonging to the left-side and right-side groups are selected by checking in the defect class selection window 505 (step S71). It is also possible to check both L and R. Symbols of the defect classes are displayed in nodes located on the left and right sides of the selected branch point in the tree structure display window 501 according to the selection result. Subsequently, a defect feature to be used is selected by a check on the left side of the defect feature name in the feature distribution display window 506 (step S72). Subsequently, a discriminant reference is set by using the discriminant reference setting GUI displayed by depressing the "detail" button 508 (step S73).

Figure 9:
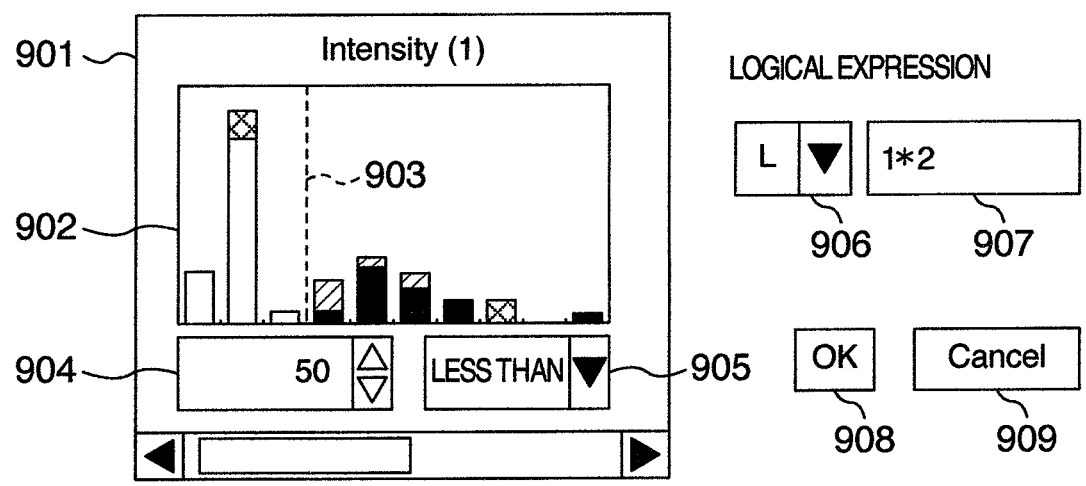
FIG. 9 is a diagram showing an embodiment of a GUI for manually setting a discriminant reference, according to the present invention.

FIG. 9 is a diagram showing an embodiment of the discriminant reference setting GUI using the user interface unit 113. Reference numeral 901 denotes a threshold setting window. A histogram by classes 902 for the selected defect feature is displayed in the threshold setting window 901. A defect feature name with a serial number in the range of 1 to N added thereto is displayed above the histogram 902. Here, N is the number of selected defect features.

A line 903 represents a threshold, and it is linked to a value displayed in a window 904. In the window 904, the value can be changed by taking a section of the histogram as the unit and using a spin button. In a window 905, either "less than the threshold" or "at least the threshold" is selected. A condition concerning one feature is thus set. In this embodiment, the condition having the serial number 1 becomes true if the "intensity" is less than 50. In a window 906, either L or R is selected. In a window 907, a logical expression representing a condition under which a defect is classified into the group selected in the window 906 is described. Each of numerical values corresponds to the serial number of the selected feature, and "*" represents a logical product. It is also possible to use "+" representing a logical add and parentheses. By depressing an "OK" button 908, a discriminant reference is set according to input and the original screen is restored. By depressing a "cancel" button 909, the original screen is restored without changing anything.

Figure 10:
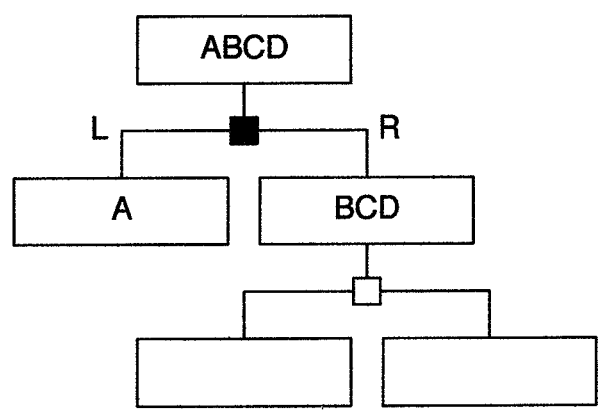
FIG. 10 is a diagram showing an embodiment of display of a tree structure on the way of setting a classify condition for constructing (generating) a sorter having a binary tree structure according to the present invention.

The branch condition can thus be set with respect to the selected branch point. The correct answer ratio is calculated according to the defect class selection and the discriminant reference setting and displayed in the evaluation window 509. This branch condition is registered by depressing the "register" button 512. As for the display in the tree structure display window 501 at this time, a new branch point is displayed under a node to which a plurality of defect classes belong, for example, as shown in FIG. 10. In this state, the "register" button is prevented from being depressed in order to prevent an incomplete sort condition from being registered. Therefore, it is necessary to select the newly added branch point and set a branch condition according to a similar procedure. If the second branch point or a subsequent branch has been selected, defect classes that do not belong to a node located right above are prevented from being checked in both L and R in the defect class selection window 505. The histogram displayed in the feature distribution display window 506 is calculated except defects in defect classes that do not belong to the right above node and defects that are not sorted into the right above node according to the branch condition.

The contents displayed in the evaluation window 509 are also calculated except defects in defect classes that do not belong to the right above node and defects that are not sorted into the right above node according to the branch condition, in the same way. Until addition of a branch point is finished, i.e., until a tree structure in which only one defect class belongs to every terminal node is constructed, the above-described condition setting is repeated. The tree structure and branch conditions at respective branch points are registered as branch conditions by depressing the "register" button 512.

In the above-described procedure, automatic setting of a branch condition is possible for the selected branch point or every branch point following the selected branch point. The "set automatically" button 510 can be depressed in any state. The execution mode 1 can be selected at any time. Processing conducted when the mode 1 has been selected will be described later. The execution mode 2 can also be selected at any time. All the steps S71 to S73 are executed automatically. The execution mode 3 can be selected when selection of defect classes belonging to L and R has already been conducted by checking in the defect class selection window 505. The execution mode 4 can be selected when selection of a feature has already been conducted by checking in the feature distribution display window 506.

Figure 11:
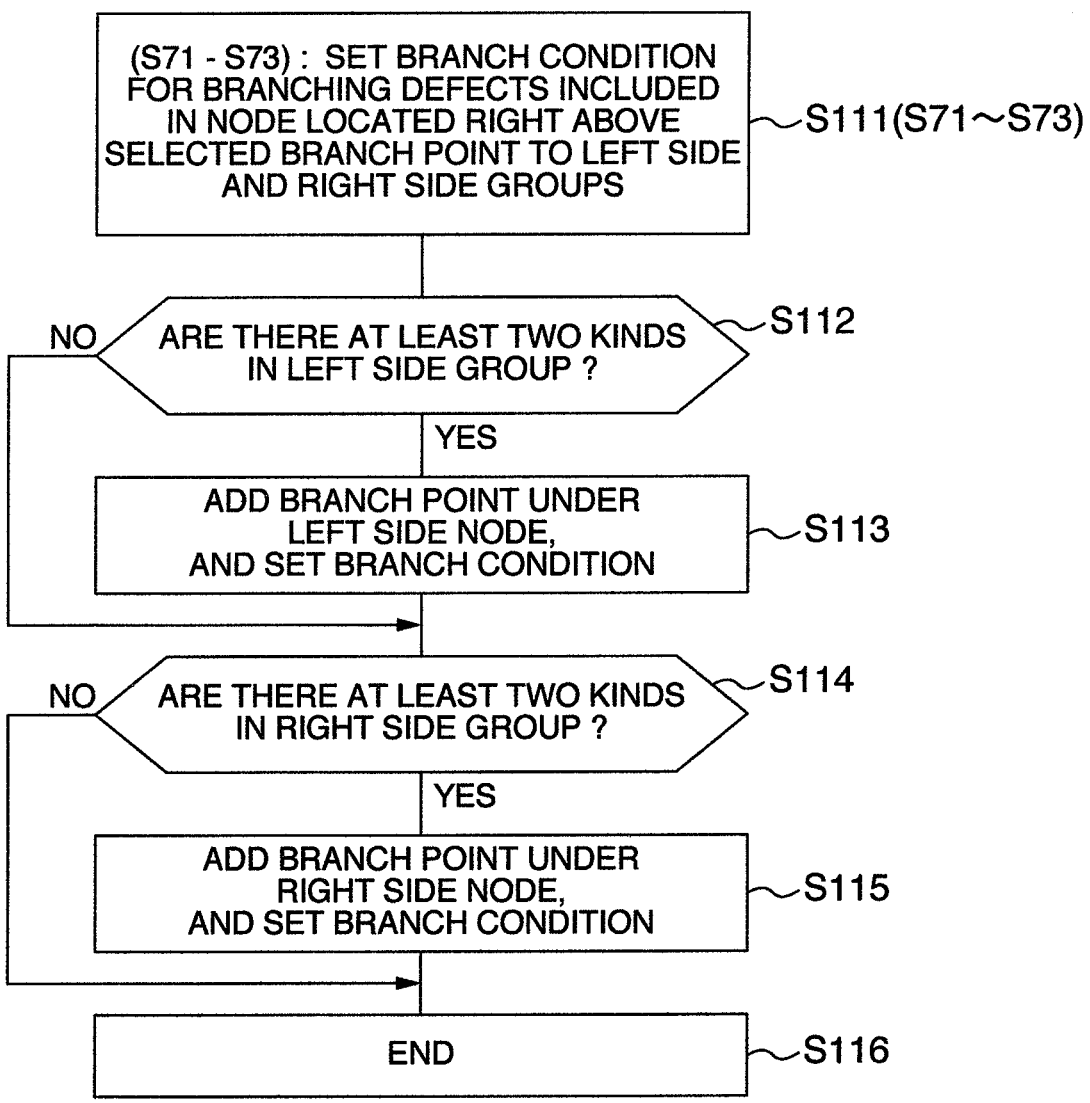
FIG. 11 is a diagram showing an embodiment of a flow of processing for automatically setting a branch condition following a branch point selected to construct (generate) a sorter having a binary tree structure according to the present invention.

FIG. 11 is a diagram for explaining a flow of processing conducted in the branch condition setting unit 111 when the mode 1 has been selected. First, a branch condition for branching defects included in a node located right above a selected branch point to left side and right side groups (S111). This corresponds to automatically executing the steps S71 to S73. If defect classes belonging to the left side group are at least two kinds (S112), a branch point is added under the left side node and a branch condition is set (S113).

This corresponds to executing the step S111 to step S116 recursively.

If a defect class of one kind belongs to the left side group at step S112, the step S113 is skipped. If defect classes belonging to a right side group are at least two kinds at step S114, a branch point is added under the right side node and a branch condition is set (S115).

Processing conducted at the step S115 is processing similar to that conducted at the step S113. If a defect class of one kind belongs to the left side group at the step S114, the step S115 is skipped. The processing is thus finished (S116). Although not illustrated, pruning may be conducted by using the known method after the binary tree is constructed by using the above-described method.

Figure 12A:
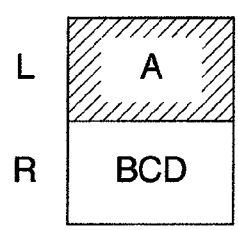
FIGS. 12A-12F are a diagram for explaining an algorithm that automatically sets a branch condition for constructing (generating) a sorter having a binary tree structure according to the present invention.
Figure 12B:
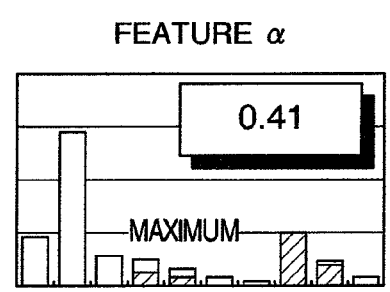
Figure 12C:
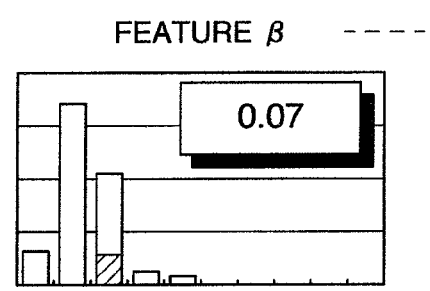
Figure 12D:
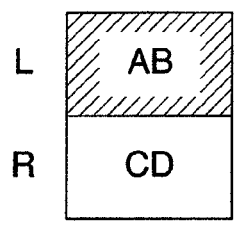
Figure 12E:
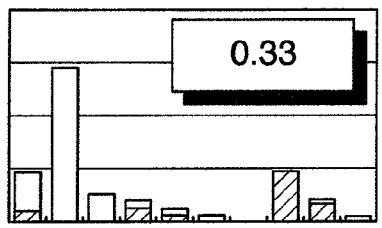
Figure 12F:
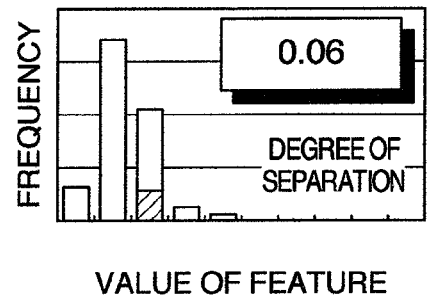
Figure 14:
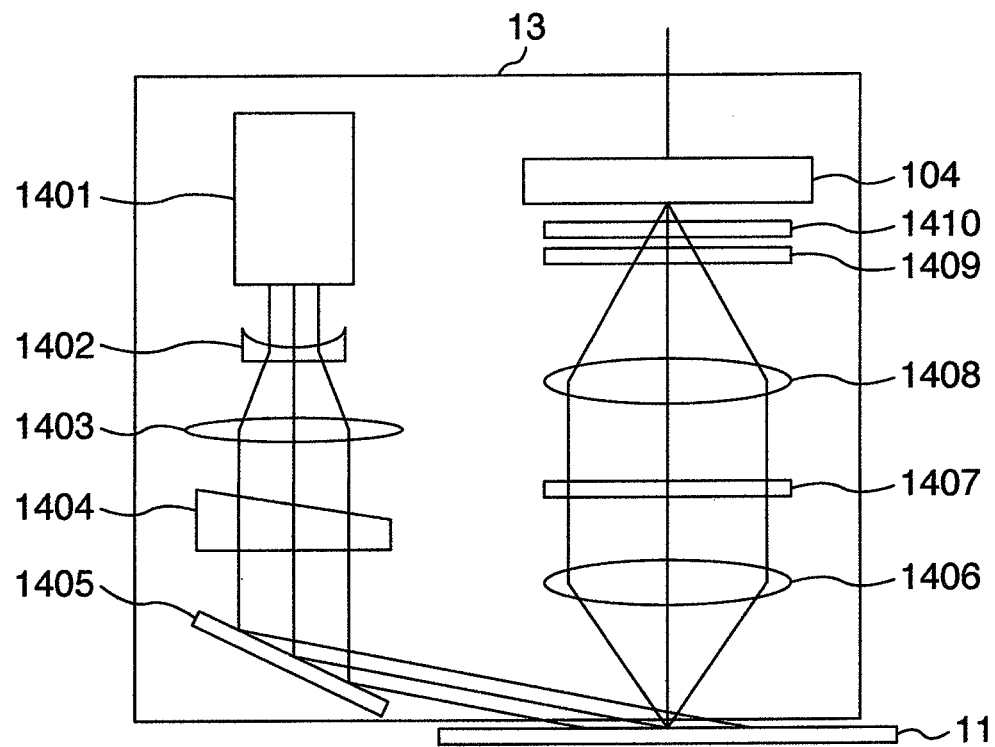
FIG. 14 is a diagram showing another embodiment of a detection unit in a defect inspection apparatus (visual inspection apparatus) according to the present invention.

An algorithm for automatically executing the steps S71 to S73 will now be described with reference to FIGS. 12A-12F. FIGS. 12A-12F show an embodiment at the time when "rule base" has been selected as an algorithm. First, the degree of separation is evaluated with respect to all combinations in dividing existing defect classes into L and R and all features. A way of dividing defect classes that yields the highest degree of separation is selected (step S71) and a feature is selected (step S72). In FIGS. 12A and 12D, the ordinate indicates the way of dividing defects into L and R, and the abscissa indicates the feature. FIGS. 12B, 12C, 12E and 12F show histograms of features by L and R, and the degree of separation calculated on the basis thereof. For evaluation of the degree of separation, for example, the difference in entropy between before and after feature observation is used. The entropy is high in a state in which groups to be divided are mixedly present, whereas the entropy becomes low in a state in which the groups have been separated. The Mahalanobis distance, the entropy gain ratio, the GINI index, the Kullback information content, or the like may be used to evaluate the degree of separation. Subsequently, a threshold that maximizes the chi-square statistics with respect to the way of division and feature of the selected defect classes is found. It is checked whether L is less than the threshold or at least the threshold, and it is used as a discriminant reference (step S73). It is also possible to calculate the correct answer rate (accuracy) for each class, and cause a defect to belong to both L and R when the correct answer ratio is lower than a reference value previously set as a parameter. Also when "FV (fuzzy voting)" is selected as the algorithm, processing as far as the step S72 is conducted in the same way as that described above. In the same way of dividing defect classes, a plurality of defect features such as the second degree of separation and the third degree of separation may also be selected. At the step S73, a likelifood function by classes is found for each of defect features selected on the basis of the histogram and used as a discriminant reference. Besides, a discriminant technique suitable for two classes, such as the support vector machine (SVM) or the linear discriminant method, may also be applied. At that time, all features may be used without especially conducting the feature selection. As for the evaluation of the degree of separation, a result obtained by conducting the sorter learning and evaluating the correct answer ratio may be used. Any method may be used as long as it is predetermined for the algorithm which becomes the selection subject or it can be set by a parameter.

If the execution mode 2 in the automatic setting has been selected, the steps S71 to S73 are executed only once by using a technique similar to that described above. If the execution mode 3 has been selected, processing is executed from the step S72. However, evaluation of the degree of separation is conducted on only a specified way of dividing, and a defect feature maximizing the degree of separation is selected. However, defect classes checked in both L and R are previously excluded from the calculation of the degree of separation. If the execution mode 4 is selected, only the step S73 is executed automatically.

If the classify condition setting GUI according to the present invention is used, it is possible to change the threshold after the automatic setting has been conducted. Furthermore, it is also possible to add a branch point after the automatic setting has been conducted. It becomes means for approaching the goal when the purity is low. Its method will now be described. First, the "set automatically" button 510 is selected at the time of start of the classify condition setting shown in FIG. 9. Then, the execution mode 1 is selected in an automatic setting mode setting window 601. As a result, all tree structures and branch conditions are set automatically. Thereupon, the tree structure and the evaluation results as shown in FIGS. 5A, 5B and 5C are displayed.

Here, the number of defect classes included in L is made large, if the purity in L is low. For example, L in the class C is also checked. Thereupon, A and C are displayed in the left side node, and a new branch point is added under the left side node. The added branch point is selected, and a branch condition for division into A and C is set by automatic setting or manual setting. On the contrary, if the accuracy in L is judged to be insufficient, R in the class A is also checked. All classes A, B, C and D are displayed in the right side node. The branch point under the node and the following are set again automatically or manually. According to the present invention, it thus becomes possible to set the classify condition with a user's intention reflected. For example, it thus becomes possible to set the classify condition with a user's intention of conducting adjustment so as to make the purity and/or accuracy of important defects at least target values reflected, with a user's intention of avoiding use of a certain feature intentionally reflected, or with a user's intention of determining features to be used on the basis of knowledge reflected.

As for the defect feature data displayed in the feature distribution display window 506, the output of the feature extraction unit 109 is used as it is, in the foregoing description. However, it is favorable to previously standardize each defect feature by using the expression $x=(x-\mu)/\sigma$. Here, x is the value of a defect feature, $\mu$ is its average, and $\sigma$ is its standard deviation. If a defect feature is not zero, the correct answer ratio is improved in some cases by raising the value of the defect feature to $\lambda$th power, where $\lambda$ is a real number which is 1 or less and which is not 0, thus converting the scale, and then conducting standardization. Or it is favorable in some cases to use a defect feature subjected to axial transformation using the principal component analysis or the like. It is also possible to use defect features with a new defect feature added by conducting some arithmetic operation such as finding a ratio between defect features.

It is desirable to conduct such transformation and addition of defect features before setting the classify condition using the classify condition setting GUI. Or although not illustrated, it is also possible to use a configuration in which scale transformation and axis transformation can be conducted by operation on the feature distribution display window 506.

In the foregoing description, defect class information is output from the review apparatus 16. Alternatively, it is also possible to use a configuration in which the defect coordinates, the inspected image and the review image shown in FIG. 4 with parentheses are collected in the sort condition setting unit 111 and instruction data are generated by visualization sort.

FIGS. 13A-13D show an embodiment of a defect instruction GUI using the user interface unit 113 for displaying the inspection image and the review image and conducting visual classification in the sort condition setting unit 111. Maps representing defect positions on a wafer and a die are displayed on a wafer map display window 1301 (FIG. 13A) and a die map display window 1302 (FIG. 13B), respectively. Inspection images for respective defect classes are displayed in an inspection image display window 1303 (FIG. 13C) in the order of the defect ID. Every defect is displayed in a row of some class or a row represented as "unsorted" without duplication. By drug and drop of an image, a defect class of the corresponding defect can be instructed. A defect image 1305 and a reference image 1306 of the selected defect obtained in the inspection apparatus and a defect image 1307, a reference image 1308 and a feature list 1309 obtained in the review apparatus are displayed in an inspection information detail display window 1304 (FIG. 13D). The defect selection is conducted by clicking a defect point on the wafer map, clicking a defect point on the die map, or clicking an inspection image in the inspection image display window 1303. According to this method, it is possible to instruct a defect class even for a defect that is not reviewed, on the basis of the inspection image. Unless a defect can be discriminated, it should be left in the "unsorted" row. Therefore, the number of instruction samples can be increased. As a result, correct sort condition setting becomes possible. It is desirable to store results obtained by thus conducting the visualization sort in the storage 112 as feature data with class information.

In the present embodiment, defect class codes instructed first are assigned different symbols. However, it is also conceivable to provide an editing function for the defect class list 503 and make it possible to handle a plurality of defect classes as one defect class. If the present function is used, improvement of the classify correct answer ratio can be anticipated by handling a plurality of classes that are difficult to separate as one class.

The visual inspection method, and apparatus, according to the present invention are not restricted to the visual inspection apparatus in the present embodiment. For example, even if the detection unit 13 is the dark field of vision type or the SEM type, the sort condition setting can be conducted by using a similar configuration. An embodiment of a configuration in which a dark vision field optical system is used as the detection unit 13 and light is applied obliquely and light scattered from the subject is detected in the upper part will now be described with reference to FIG. 14. Light emitted from a laser light source 1401 is formed in a slit form by a beam expansion optical system including a concave lens 1402 and a convex lens 1403, a circular cone lens (including a pseudo circular cone lens having a cylindrical lens inclined about the optical axis), and a mirror 1405, and resultant light is applied to a wafer 11 obliquely. The reason why the irradiation light is formed in the slit form is that inspection speed is raised. The detection optical system for detecting the scattered light on the surface of the wafer 11 includes a Fourier transform lens 1406, a spatial filter 1407, an inverse Fourier transform lens 1408, an ND filter 1409, an optical filter 1410 such as a sheet polarizer, and an image sensor 104. The spatial filter 1407 is placed on a Fourier transform plane to shield diffracted light arriving from a repeated pattern on the wafer. On the other hand, scattered light from a defect is spread on the Fourier transform plane irregularly, and consequently most thereof is received by the image sensor 104 without being shielded. Therefore, the S/N is improved, and it becomes possible to detect the defect with high sensitivity. A signal detected by the image sensor 104 is input to the image processing unit 14. The defect detection, the image cropping, the feature calculation and the defect classification are conducted by using a method similar to the above-described method. Operation in the sort condition setting unit 111 is conducted in the same way. The configuration in the present embodiment has one sensor 104 for image detection. As an alternative configuration, it is also possible to provide a detection optical system for conducting detection from different angles, conduct image detection by using two or more sensors, use feature data obtained by defect detection, image cropping and feature extraction together, and thereby conduct defect sort. As another alternative configuration, it is also possible to conduct inspection twice or more times under different optical conditions, conduct coordinate matching of the detected defects, use obtained feature data together, and classify defects. As another alternative configuration, a classify condition may be individually set by using feature data obtained under respective inspections. In other words, the case where the inspection condition (including the optical condition) is changed is also included as obtained feature data.

When executing the inspection, the configuration conducts classification according to the classify condition corresponding to the inspection condition, adds reliability information of the defect class such as the purity of the defect class (calculated when setting the sort condition) to the defect class, and determines a defect class for each of the detected defects by applying a majority decision or a reliability weighted majority decision to defect classes added in a plurality of inspections.

In the foregoing description, the visual inspection conducted by comparing wafers on which patterns taking the same shape are formed has been taken as an example. However, the classify condition setting method according to the present invention can also be applied to inspection of a wafer having no patterns.

Figure 15:
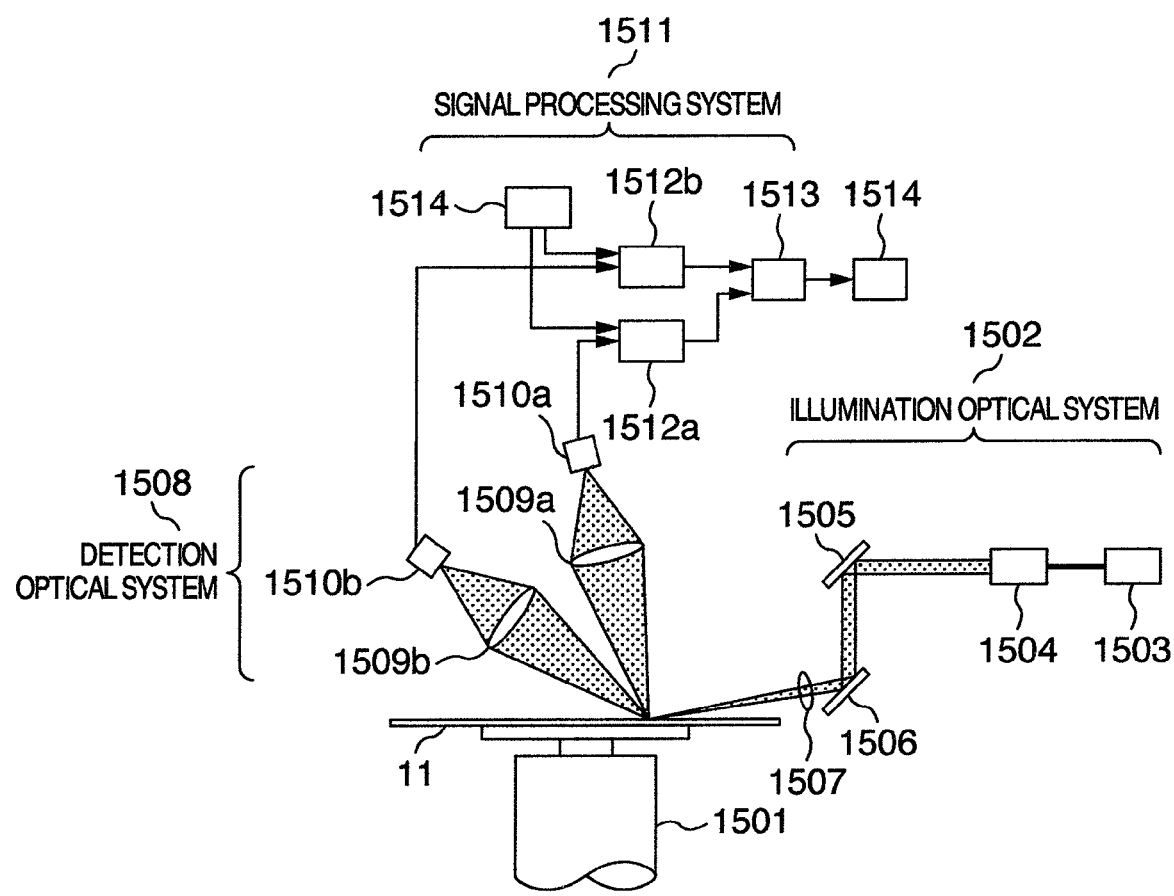
FIG. 15 is a schematic configuration diagram showing another embodiment of a defect inspection apparatus (visual inspection apparatus) according to the present invention.

An embodiment of a configuration of a defect inspection apparatus (visual inspection apparatus) for wafers having no patterns will now be described with reference to FIG. 15. A semiconductor wafer 11 which is the subject is retained by a rotational stage 1501. An illumination optical system 1502 includes a laser light source 1503, a beam expander 1504, mirrors 1505 and 1506, and a condenser lens 1507. A detection optical system 1508 includes condenser lenses 1509a and 1509b, and photoelectric converters 1510a and 1510b. A signal processing system 1511 includes threshold processing units 1512a and 1512b, a defect discriminant unit 1513 and a threshold by area setting unit 1514. An inspection method implemented in the inspection apparatus shown in FIG. 15 will now be described. A laser beam emitted from the laser light source 1503 is expanded in beam diameter by the beam expander 1504, then narrowed down in beam diameter by the condenser lens 1507 via the mirrors 1505 and 1506, and applied onto the wafer 11. If a defect such as a dust particle is present in a beam irradiation position on the surface of the wafer 11, strong scattered light is generated. The scattered light is condensed onto a light sensing plane of the photoelectric converter 1510a by the condenser lens 1509a, and subject to photoelectric conversion by the photoelectric converter 1510a. Scattered light is detected by the condenser lens 1509b and the photoelectric converter 1510b which are disposed at a different angle, in the same way. The direction in which strong scattered light is generated differs depending upon the size and shape of the defect. Therefore, the sensitivity can be improved by conducting detection from a plurality of angles. In addition, it is more desirable to increase the detection system so as to cover all orientations. Outputs of the photoelectric converters 1509a and 1509b are compared with a threshold in the threshold processing units 1512a and 1512b. If an output is greater than the threshold, it is detected as a defect. Detection signals of the threshold processing units 1512a and 1512b are input to the defect discriminant unit 1513, and defect sort is conducted on the basis of magnitudes of the signals and a ratio between the signals. For inspecting the whole surface of the wafer 11, it is necessary to scan the wafer 11 with the irradiation position of the laser beam. Spiral scanning is made possible by causing a straight movement of the rotation axis so as to make the rotation axis approach the irradiation position while rotating the wafer 11 by using the rotational stage 1501. If scanning the wafer 11 in the radius direction with the laser beam is used in combination with the straight movement although not illustrated, a straight movement corresponding to the width of the scanning with the laser beam can be made during one revolution, and consequently the time required to inspect the whole surface of the wafer can be shortened. Instead of scanning with the laser beam, a slit-like beam which is long in the radius direction of the wafer 11 may be formed and applied by using a cylindrical lens or a circular cone lens, although not illustrated. The sort condition can be set according to the above-described method by using magnitudes and ratios of signals detected by a plurality of detectors as feature data.

Second Embodiment

A second embodiment of a defect classification method, and apparatus, and a defect inspection method, and apparatus, in which defects are classified by using a classifier constructed (generated) with a classify condition setting function according to the present invention will be described in detail with reference to FIGS. 16 to 22.

The second embodiment according to the present invention differs from the first embodiment in that the second embodiment has a function of specifying user's intention (target performance of purity and accuracy for each defect class, the whole and the worst case) with a priority order and a function of evaluating performance of sort according to the preset sort condition and displaying whether the specified target performance is satisfied, for each item intended by the user.

The defect inspection apparatus (visual inspection apparatus) according to the second embodiment has a configuration similar to that of the first embodiment. By the way, the defect classify unit 110 according to the present invention conducts classification by using the classify condition preset in the classify condition setting unit 111 and outputs class information of each defect.

As for the defect classify unit 110 in the second embodiment, the case where defects are classified by using a classifier having a binary tree structure on the basis of features of the defects described with reference to the first embodiment and the case where defects are classified by using a classifier of instruction type on the basis of features of the defects are conceivable. When the classifier having the binary structure is used, the classify condition setting unit 111 displays whether each of items of the user's intention is satisfied with respect to a specified branch point. Here, the user's intention is, for example, a desire to give priority to raising accuracy or purity for a specific defect over the correct answer ratio of the whole.

If a classifier of instruction type is used, any algorithm may be used as long as it is a learning algorithm (classify algorithm of instruction type). In addition, it is more desirable to prepare a plurality of learning algorithms and make them selectable.

Figure 16:
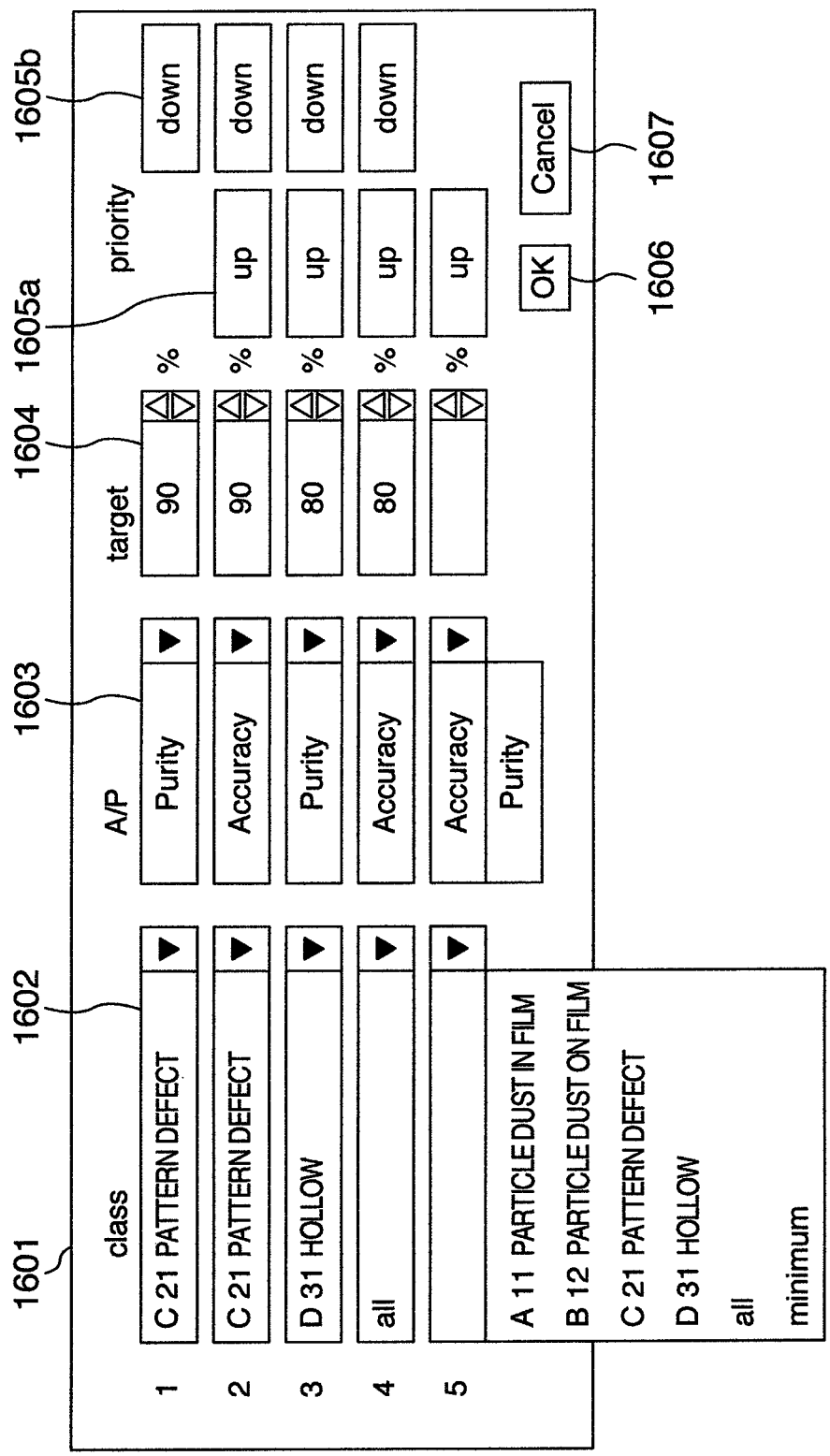
FIG. 16 is a diagram showing a second embodiment of a GUI for specifying user's intention with priority orders in a sort condition setting unit included in classifier construction means according to the present invention.

FIG. 16 shows an embodiment of a GUI using a user interface unit 113 for specifying user's intention with priority orders in a classify condition setting unit 111. In a priority order specifying window 1601, a defect class, selection of accuracy or purity, and target sort performance are specified in association with a priority order. As for the defect class, it is selected from a defect class selection list 1602 and specified. Class codes and class names of all kinds included in the instruction data, "all," and "minimum" are included in the list. Here, "all" represents the correct answer ratio of all defects, and "minimum" represents the worst value of accuracy or purity of each class. Accuracy or purity is selected in an accuracy/purity selection list 1603. Target performance is set by inputting a numerical value to a target setting window 1604. Since setting is conducted basically in order from the highest priority order, a new item can be input only in a row located right under an already set item. After the setting, the priority order can be changed by using priority order change buttons 1605a and 1605b. If "up" is pressed, the item is interchanged with an item located right above. If "down" is pressed, the item is interchanged with an item located right under. When desiring to insert a new item, the item is input to the bottom row and then moved to a location desired to be inserted in by using the "up" button. Depressing an "OK" button causes input setting to be stored and the processing to be ended. Depressing a "cancel" button causes input setting to be discarded and the processing to be ended.

Figure 17:
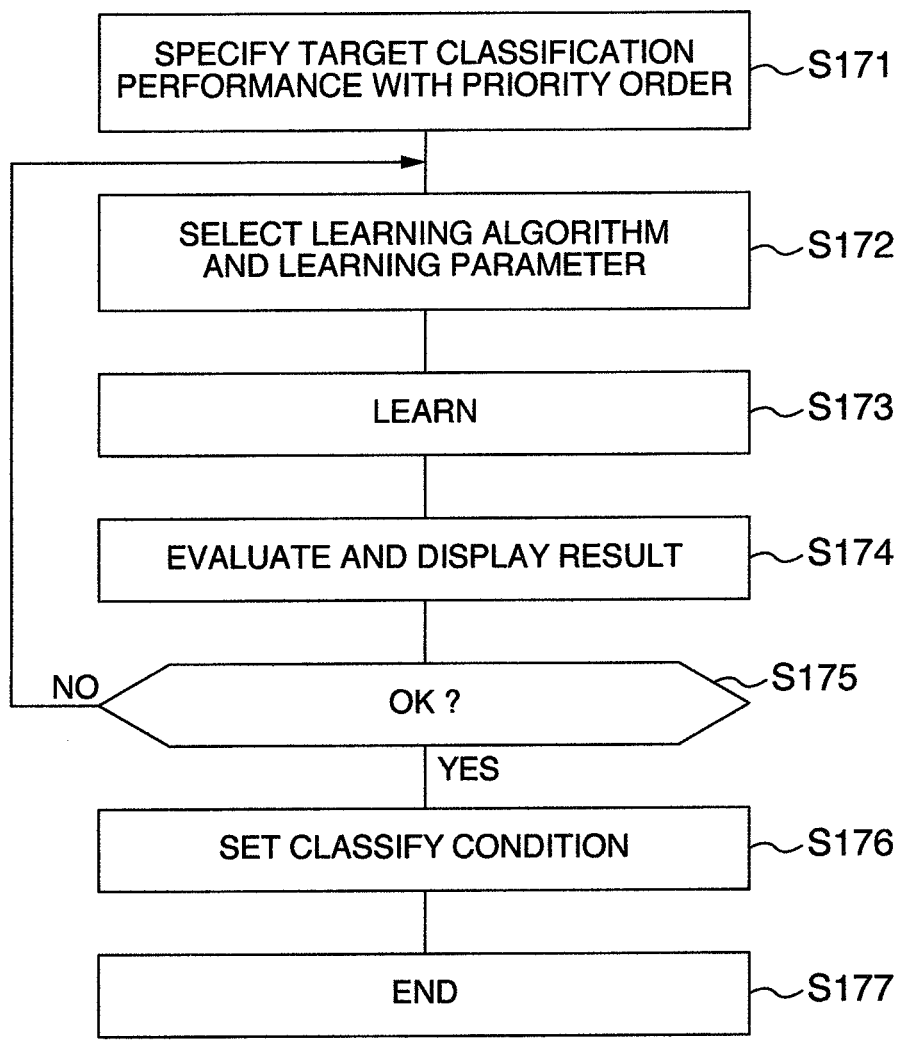
FIG. 17 is a diagram showing an embodiment of a classify condition setting flow for constructing (generating) a classifier (classify algorithm) of instruction type other than the binary tree structure according to the present invention.

A classify condition setting flow in the case where a classify algorithm of instruction type (sorter of instruction type) other than the binary tree structure is used according to the second embodiment of the present invention will now be described with reference to FIG. 17. First, target classification performance by items is specified with a priority order by using the GUI shown in FIG. 16 (S171). Subsequently, the classify condition of the classifier of instruction type is set by learning using a learning algorithm and a leaning specified (selected) previously at step S172, on the basis of instruction of the defect class and defect feature data associated therewith (S173). Then, classification performance according to the set classify condition is evaluated (S174). As for the evaluation method, the leave one out method is desirable. In the leave one out method, one sample is used as a test sample whereas remaining samples are used as instruction samples and the evaluation is repeated by the number of defects. The evaluation result is displayed together with degrees of satisfaction of the user's intention specified by the GUI (S174).

FIG. 18 shows an embodiment of a GUI using the user interface unit 113 for displaying the degrees of satisfaction of the user's intention. A satisfaction degree evaluation display window 1702 and a confusion matrix 1703 are displayed in an evaluation result display window 1701. The satisfaction degree evaluation display window 1702 and the confusion matrix 1703 display the same result with different visual points. The defect class, selection of accuracy or purity, target performance, performance evaluation result, difference from the target, and decision are displayed in the satisfaction degree evaluation display window 1702 in the order of priority order. The confusion matrix 1703 shows an aggregate which indicates defect classes defects are classified into under the classify condition learned about instructed correct answer defect classes.

The accuracy, i.e., the correct answer ratio for each of defect classes under the learned sort condition is displayed in the rightmost column. The purity, i.e., the ratio of the number of defects sorted correctly to defects sorted into a certain defect class by the learned classify condition is displayed in the bottom row. The correct answer ratio of the whole is displayed in the right bottom corner. With respect to each of items specified as to the target sort performance, the priority order and a decision (represented by "○" or "×") are displayed to the right of the accuracy or under the purity. It is possible to obtain information as to a defect class in which an error is apt to occur by displaying the confusion matrix. If it is judged that "OK" should be given on the basis of the evaluation result (S175), then a classify condition is set by learning using all instruction data in response to depression of a "register" button 1704 (S176), the classify condition is registered in the storage 112, and the processing is finished (S177). If the result is judged to be NG, then the processing returns to the step S172, or the processing is finished without conducting anything by depressing an "end" button 1705.

Figure 19:
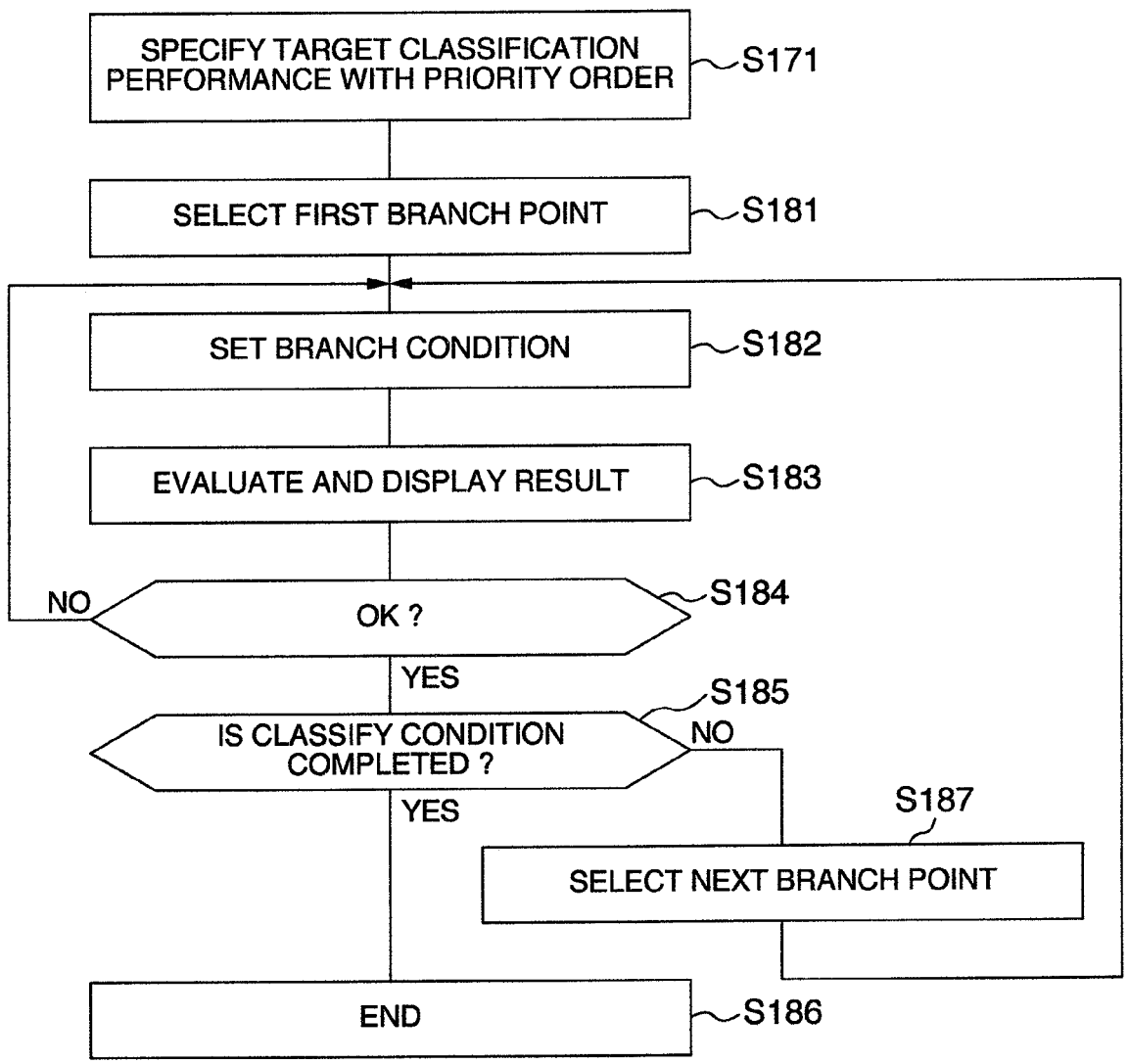
FIG. 19 is a diagram showing an embodiment of a classify condition setting flow for constructing (generating) a classifier having a binary tree structure according to the present invention.

A classify condition setting flow in the case where a classifier having a binary tree structure is used according to a second embodiment of the present invention will now be described with reference to FIG. 19. First, target classification performance by items is specified with a priority order by using the GUI shown in FIG. 16 (S171). Subsequently, a first branch point is selected on the tree structure display window 501 in the GUI shown in FIG. 5 (S181). With respect to the selected branch point, a branch condition is set by using the GUI shown in FIG. 5 (S182). Subsequently, evaluation is conducted and its result is displayed (S183). In other words, target performance of purity and accuracy for each defect class, the whole and the worst case is specified previously with a priority order (S171). After the branch condition is set, it is evaluated for each item whether the specified target sort performance is specified and its result is displayed (S183).

FIGS. 20A and 20B show an embodiment of a GUI for displaying whether each item is satisfied with respect to the specified branch point. FIGS. 20B and 20C are different from FIGS. 5B and 5C in that target classification performance by items is displayed in a window 1801 and a column of "Opp" (abbreviation of "opposite") which belongs to an opposite group at an upstream branch point is provided. In FIG. 20A, the first branch point has been selected. Therefore, a defect class belonging to "Opp" is not present, and a defect classified to "Opp" is not present, either. Furthermore, in the same way as FIG. 18, a priority order (represented by a numeral surrounded by a rectangle) and a decision (represented by "○" or "×") are displayed to the right of the accuracy or under the purity with respect to each of items specified as to the target sort performance.

However, items that cannot be evaluated such as the purity of the defect C or D are not displayed. Although other windows and buttons are not illustrated, they are arranged suitably.

It is determined whether "OK" should be given on the basis of the evaluation result (S184). If the result is NG, then the processing returns to the step S182. Viewing the evaluation result, it is appreciated that the accuracy of the defect C (priority order is the second) does not satisfy the target. An embodiment in which the branch condition is modified on the basis of this information is shown in FIGS. 21A and 21B. First, as shown in FIG. 21A, the defect C is added as the defect class belonging to L, and a change is made so as to divide the defects into AC and BCD. Thereupon, evaluation results change as shown in FIG. 21A. Since the defect C belongs to both L and R, the defect C may be sorted into any of them and the accuracy becomes 100%. At this time point, an item having NG (×) disappears. As shown in FIG. 21B, therefore, the next branch point is selected, a branch condition is determined manually or automatically, and display contents of the evaluation window 509 is updated. The L column indicates defects sorted into the defect A and the purity can be evaluated. Since the target performance is not specified, however, it is not displayed. The R column indicates defects classified into the defect C. At this time, calculation is conducted supposing that defects belonging to "Opp" can be classified perfectly so as to facilitate the decision as to whether the branch condition at the selected branch point is good. In other words, the best case is evaluated. For example, since the defect C belongs to "Opp" as well, it is supposed when calculating the purity that the defect C on the "Opp" side can be sorted with 100% in both accuracy and purity. Furthermore, the correct answer ratio of the whole is also calculated supposing that defect classes (parts of B and C, and D) belonging to "Opp" are 100% in correct answer ratio.

Therefore, it is appreciated that the purity (priority order is first) of the defect C does not satisfy the target even in the best case. In order to satisfy the target, it becomes necessary to change the discriminant of A and C, or add A as a defect class belonging to R and further increase branch points. If the evaluation result is judged to be OK (S184), then it is checked whether the branch condition is completed, i.e., the tree structure is completed (S185). If the tree structure is completed, then the tree structure and the branching condition at each branch point is registered as the branching condition and the processing is finished (S186). If the tree structure is incomplete, the next branch point is selected (S187) and the processing returns to the step S182.

It becomes possible to conduct modification for satisfying the target easily by thus evaluating and displaying whether the target is satisfied at each branch point by using the classifier having the binary tree structure.

As heretofore described, the user conducts algorithm selection and parameter setting which are the sort condition of the classifier, and whether the user's intention is satisfied and the difference from the target classification performance are displayed. As a result, the function of supporting the optimum algorithm selection and parameter setting can be provided.

Figure 22:
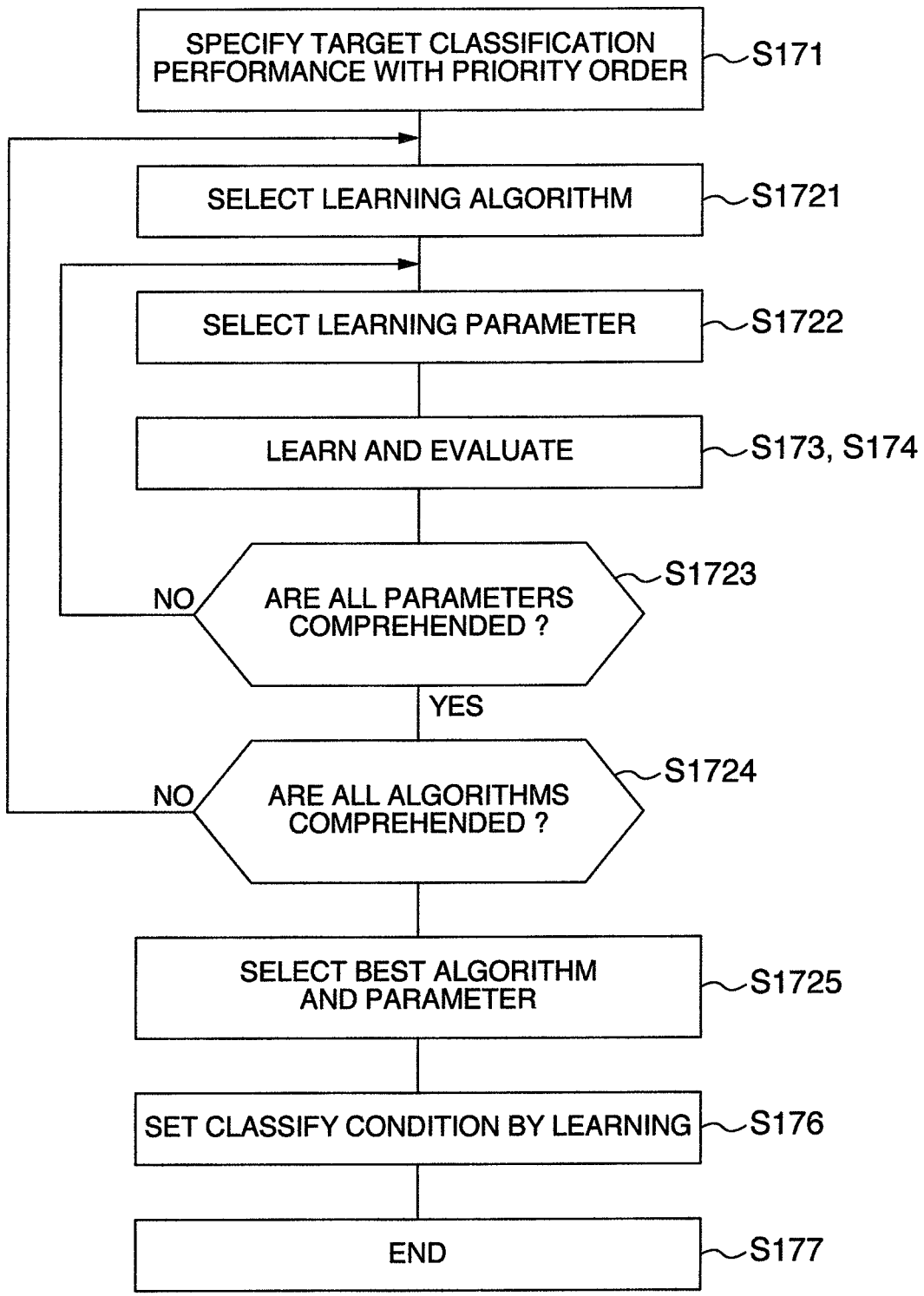
FIG. 22 is a diagram showing an embodiment of a flow for evaluating satisfaction of a user's intention while conducting algorithm selection and parameter setting automatically and comprehensively and searching for an algorithm and a parameter that make the satisfaction the highest, in classify condition setting for constructing (generating) a classifier (sort algorithm) of instruction type according to the present invention.

Here, it is also conceivable to use a configuration for evaluating the degree of satisfaction of the user's intention while conducting the learning algorithm selection and the learning parameter setting automatically and comprehensively and searching for an algorithm and a parameter that make the degree of satisfaction the highest. FIG. 22 shows its flow. In the same way as the foregoing description, target classification performance by items is specified with a priority order by using the GUI shown in FIG. 16 (S171). Learning algorithm selection (S1721) and learning parameter setting (S1722) are conducted. Learning is executed, and the degree of satisfaction of the user's intention is evaluated (S173 and S174). If all parameters are not comprehended (S1723) or if all algorithms are not comprehended (S1724), the processing returns to the step S1722 or S1721. The degree of satisfaction of the user's intention is first evaluated on the basis of the number of items that have satisfied the target classification performance without defeat from the highest priority order. In other words, supposing that the priority orders 1 to 5 are specified, the case where only the priority order 1 is satisfied is judged to be higher in degree of satisfaction than the case where the priority orders 2 to 5 are satisfied. If the numbers of items that have satisfied the target classification performance without dissatisfaction from the highest priority order are the same, then evaluation is conducted on the basis of the numbers of items that have satisfied the target classification performance. If this is also the same, evaluation is conducted by using the correct answer ratio of the whole. Alternatively, evaluation is conducted by using the performance of the item having the highest priority order, or evaluation is conducted by using the worst value of the accuracy and purity for all defect classes. Various evaluations are thus conceivable. However, any valuation may be used as long as it is predetermined. It is also possible to prepare some evaluation viewpoints, display results judged to be the best from respective viewpoints, and make the user conduct selection. The best algorithm and parameter are selected (S1725). The classify condition is set by learning using all instruction data (S176). The classify condition is registered in the storage 112 and the processing is finished (S177). In other words, when to classify defects by using a classifier of instruction type on the basis of features of the defects, target performance of purity and accuracy for each defect class, the whole and the worst case is specified previously with a priority order (S171). While comprehensively changing the learning algorithm and the learning parameter on the basis of instruction of defect feature data previously associated with defect classes, it is evaluated item by item whether the specified target classification performance is satisfied. The learning algorithm and learning parameter that are favorable in evaluation result are searched for (S1721 to S1725 and S174). The classify condition of the classifier is set by learning the learning algorithm and learning parameter obtained by the search (S173 and S176).

According to the present invention, in construction (generation) of the binary tree structure, condition setting at each branch point of the classifier having the binary tree structure is conducted automatically and manual setting is conducted for only a selected branch point and the subsequent structure. As a result, it becomes possible to set the classify condition with the user's intention reflected, without requiring labor for conducting all setting manually. The user's intention is, for example, to conduct adjustment so as to make the purity and/or accuracy of important defects equal to at least a target value, to intentionally avoid use of a certain feature, or to determine a feature to be used, on the basis of knowledge.

Furthermore, according to the present invention, it becomes possible in construction (generation) of the classifier of instruction type to set the classify condition with the user's intention reflected.

Furthermore, according to the present invention, it becomes possible in construction (generation) of a classifier of the binary tree structure type or instruction type to set the classify condition with the user's intention reflected, by conducting specification with a priority order as the user's intention and evaluating the degree of satisfaction of the user's intention.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. A computer-implemented defect classification method to classify defects, by using a classifier constructed based on features of defects extracted from detected signals acquired from a defect inspection apparatus, the computer-implemented defect classification method comprising:
   constructing the classifier by using a classifier construction process commanded by a computer processor to set a branch condition for each of at least one branch point of the classifier, based on instruction of defect classes and feature data previously associated with the defect classes, the branch condition of each branch point including:
      one or more defect classes located on each side of the at least one branch point,
      a feature to be used to branch, and
      a discriminant reference,
   wherein the classifier construction process includes a priority order specification process configured to display a user selection panel configured to obtain the following data from a user, for each of a plurality of defect classes: a preferred parameter of one of purity and accuracy, a target performance value for said preferred parameter, and a priority ranking in comparison to other defect classes, and wherein the classifier construction process is configured to construct the classifier based on data obtained by the priority order specification process;
   using the computer processor to input unclassified defects into the classifier, receive classification results from the classifier, and store the classification results and/or exhibit the classification results via a user interface.

2. The computer-implemented defect classification method according to claim 1, wherein in the classifier construction process, a branch condition setting includes at least one of an automatic setting and a manual setting.

3. The computer-implemented defect classification method according to claim 1, wherein the classifier construction process includes a display process configured to display information that represents feature distribution by defect classes, and information that represents an evaluation result of classification performance under a set branch condition, for every branch point.

4. The computer-implemented defect classification method according to claim 3, wherein the classifier construction process includes an evaluation process configured to evaluate whether the target performance value under the set branch condition is satisfied for every item, and displaying a result of an evaluation for every item.

5. The computer-implemented defect classification method according to claim 1, wherein features used to classify defects are obtained by unifying features of defects extracted from detected signals acquired by respective inspections under a plurality of different conditions in the defect inspection apparatus, after conducting matching of defect coordinates.

6. The computer-implemented defect classification method according to claim 1, wherein when classifying defects by using a classifier constructed based on features of the defects, defect classes are determined by individually using features of the defects extracted from detected signals acquired by respective inspections under a plurality of different conditions in the defect inspection apparatus, individually making defect classification decisions according to a plurality of defect classification conditions preset for the classifier, and unifying results of individual defect classification decisions by weighted voting of reliability.

7. The computer-implemented defect classification method according to claim 1, wherein the classifier has a binary tree structure.

8. A defect classification apparatus to classify defects, by using a classifier constructed based on features of defects extracted from detected signals acquired from a defect inspection apparatus, the defect classification apparatus comprising:
 a classifier construction means configured to construct the classifier by setting a branch condition for each of at least one branch point constructed based on instruction of defect classes and feature data previously associated with the defect classes, the branch condition of each branch point including:
  one or more defect classes located on each side of the at least one branch point,
  a feature to be used to branch, and
  a discriminant reference;
 wherein the classifier construction means includes a priority order specification means configured to display a user selection panel configured to obtain the following data from a user, for each of a plurality of defect classes: a preferred parameter of one of purity and accuracy, a target performance value for said preferred parameter, and a priority ranking in comparison to other defect classes; and
 wherein the classifier construction means is configured to construct the classifier based on data obtained by the priority order specification means.

9. The defect classification apparatus according to claim 8, wherein the classifier construction means includes a display means configured to display information that represents feature distribution by defect classes, and information that represents an evaluation result of classification performance under the set branch condition, for every branch point.

10. The defect classification apparatus according to claim 9, wherein the classifier construction means includes:
 a priority order specification means configured to display a user selection panel, and to obtain the following data from a user, for each of a plurality of defect classes, regardless of whether any defect class is whole or worst case; and
 an evaluation means configured to evaluate whether the target sort performance under a set branch condition is satisfied for every item, and configured to display a result of evaluation for every item.

11. The defect classification apparatus according to claim 8, wherein the features used to classify defects by using the classifier are features extracted from detected signals acquired by respective inspections under a plurality of different conditions in the defect inspection apparatus.

12. The defect classification apparatus to classify defects according to claim 8, wherein the classifier has a binary tree structure.

13. A defect inspection apparatus including:
 a stage configured to retain a substrate to be inspected,
 an image detection unit configured to detect an image of the substrate to be inspected,
 a defect decision unit configured to detect defects, by comparing two corresponding areas formed to originally become same in shape,
 a feature extraction unit configured to extract features of the defects constructed based on an image concerning each of the defects detected by the defect decision unit,
 a defect classification unit configured to classify defects by using a classifier constructed based on the features of defects extracted by the feature extraction unit; and
 a classifier construction unit configured to construct the classifier used in the defect classification unit, by setting a branch condition for each of at least one branch point constructed based on instruction of defect classes and feature data previously associated with the defect classes, and the branch condition of each branch point including: one or more defect classes located on each side of the at least one branch point, a feature to be used to branch, and a discriminant reference,
 wherein the classifier construction unit includes a priority order specification unit configured to display a user selection panel configured to obtain the following data from a user, for each of a plurality of defect classes: a preferred parameter of one of purity and accuracy, a target performance value for said preferred parameter, and a priority ranking in comparison to other defect classes, and wherein the classifier construction unit is configured to construct the classifier based on data obtained by the priority order specification unit.

14. The defect inspection apparatus according to claim 13, wherein the classifier has a binary tree structure.

15. A defect inspection apparatus including
 a rotational stage configured to retain a substrate to be inspected,
 a signal detection unit configured to apply laser light onto the substrate to be inspected, detecting scattered light and outputting a detected signal,
 a defect decision unit configured to detect defects by comparing the detected signal detected by the signal detection unit with a predetermined threshold,
 a feature extraction unit configured to extract features of each of the defects detected by the defect decision unit,
 a defect classification unit configured to classify defects, by using a classifier constructed based on features of defects extracted by the feature extraction unit, and
 a classifier construction means configured to construct the classifier used in the defect classification unit by setting a branch condition for each of at least one branch point constructed based on instruction of defect classes and feature data previously associated with the defect classes, and the branch condition of each branch point including: one or more defect classes located on each side of the at least one branch point, a feature to be used to branch, and a discriminant reference,
 wherein the classifier construction means includes a priority order specification means configured to display a user selection panel configured to obtain the following data from a user, for each of a plurality of defect classes: a preferred parameter of one of purity and accuracy, a target performance value for said preferred parameter, and a priority ranking in comparison to other defect classes, and wherein the classifier construction means is configured to construct the classifier based on data obtained by the priority order specification means.

16. The defect inspection apparatus according to claim 15, wherein the classifier has a binary tree structure.

* * * * *